(12) United States Patent
Konishi et al.

(10) Patent No.: US 11,326,023 B2
(45) Date of Patent: *May 10, 2022

(54) AROMATIC POLYCARBONATE RESIN, METHOD FOR PRODUCING SAME, AND AROMATIC DIHYDROXY COMPOUND

(71) Applicant: Mitsubishi Chemical Corporation, Chiyoda-ku (JP)

(72) Inventors: Norikazu Konishi, Chiyoda-ku (JP); Toshiki Monden, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 25 days.

This patent is subject to a terminal disclaimer.

(21) Appl. No.: 16/714,930

(22) Filed: Dec. 16, 2019

(65) Prior Publication Data

US 2020/0115494 A1  Apr. 16, 2020

Related U.S. Application Data

(63) Continuation of application No. PCT/JP2018/022786, filed on Jun. 14, 2018.

(30) Foreign Application Priority Data

Jun. 14, 2017  (JP) .............................. JP2017-116445

(51) Int. Cl.
  *C08G 64/00*   (2006.01)
  *C08G 64/04*   (2006.01)
  *C07C 39/16*   (2006.01)
  *C08G 64/30*   (2006.01)

(52) U.S. Cl.
  CPC ............ *C08G 64/045* (2013.01); *C07C 39/16* (2013.01); *C08G 64/307* (2013.01)

(58) Field of Classification Search
  USPC .......................... 528/196, 198; 548/237, 440
  See application file for complete search history.

(56) References Cited

U.S. PATENT DOCUMENTS

| | | | |
|---|---|---|---|
| 4,446,285 A | 5/1984 | Mark et al. | |
| 4,535,191 A | 8/1985 | Mark et al. | |
| 5,336,751 A | 8/1994 | Raymond, III | |
| 5,418,317 A | 5/1995 | Raymond, III | |
| 6,323,304 B1 | 11/2001 | Lemmon et al. | |
| 2009/0117478 A1* | 5/2009 | Ogawa ................. | G03G 5/0564 430/57.1 |
| 2014/0364546 A1 | 12/2014 | Okamoto et al. | |
| 2016/0152768 A1 | 6/2016 | Zouta et al. | |
| 2018/0282541 A1* | 10/2018 | Nishihara .............. | C08G 64/04 |

FOREIGN PATENT DOCUMENTS

| | | |
|---|---|---|
| CN | 1077205 A | 10/1993 |
| ER | 1492897 A | 4/2004 |
| JP | 59-131623 A | 7/1984 |
| JP | 05-001144 A | 1/1993 |
| JP | 06-016802 A | 1/1994 |
| JP | 06-128371 A | 5/1994 |
| JP | 07013363 * | 1/1995 |
| JP | 2004-523613 A | 8/2004 |
| JP | 2006-328106 A | 12/2006 |
| JP | 2010-037380 A | 2/2010 |
| JP | 2010-077398 A | 4/2010 |
| JP | 2013-139097 A | 7/2013 |
| JP | 2016-108481 A | 6/2016 |
| JP | 2016-155957 A | 9/2016 |

(Continued)

OTHER PUBLICATIONS

JP 07013363 Asano, Masanari; A Electrophotographic Photoreceptor and Manufacture Thereof (Year: 1995).*

Extended European Search Report dated Feb. 23, 2021 in corresponding European Patent Application No. 18818637.3, 5 pages.

English translation of the International Preliminary Report on Patentability and Written Opinion of the International Searching Authority dated Dec. 26, 2019 in PCT/JP2018/022786 filed Jun. 14, 2018, 6 pages.

(Continued)

*Primary Examiner* — Terressa Boykin

(74) *Attorney, Agent, or Firm* — Oblon, McClelland, Maier & Neustadt, L.L.P.

(57) ABSTRACT

Provided is an aromatic polycarbonate resin that has not only high fluidity and thin-wall moldability but also excellent hue and transparency. The aromatic polycarbonate resin contains a structural unit derived from an aromatic dihydroxy compound and a carbonate-forming compound. A hydrolysate obtained by hydrolysis of the aromatic polycarbonate resin contains aromatic dihydroxy compounds represented by the following Formulae (2) and (3), and the content of the compound represented by Formula (2) is 250 ppm by mass or less with respect to that of the compound represented by Formula (3), wherein $R_1$ represents an alkyl group having 1 to 24 carbon atoms; $R_2$ and $R_3$ each independently represent a monovalent hydrocarbon group having 1 to 15 carbon atoms; and a and b each independently represent an integer of 0 to 4:

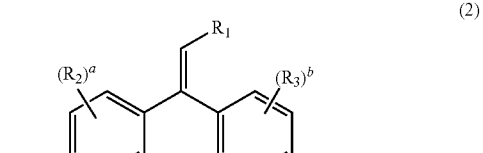

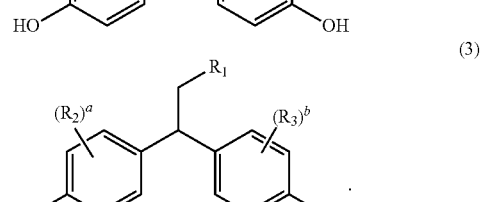

20 Claims, No Drawings

(56) References Cited

OTHER PUBLICATIONS

International Search Report dated Aug. 14, 2018 in PCT/JP2018/022786 filed on Jun. 14, 2018, 2 pages.
Office Action and Search Report dated May 7, 2021, in corresponding Chinese Patent Application No. 201880039945.0 filed Jun. 14, 2018, w/ English-language translation.

* cited by examiner

AROMATIC POLYCARBONATE RESIN, METHOD FOR PRODUCING SAME, AND AROMATIC DIHYDROXY COMPOUND

CROSS-REFERENCE TO RELATED APPLICATION

This is a continuation of International Application PCT/JP2018/022786, filed on Jun. 14, 2018, and designated the U.S., and claims priority from Japanese Patent Application 2017-116445 which was filed on Jun. 14, 2017, the entire contents of which are incorporated herein by reference.

TECHNICAL FIELD

The present invention relates to an aromatic polycarbonate resin. More particularly, the present invention relates to: an aromatic polycarbonate resin having excellent thin-wall moldability, transparency, impact strength, and bending resistance; and a method of producing the same.

BACKGROUND ART

In display devices used for personal computers, tablet PCs, smartphones and the like, planar light source devices are integrated for complying with the demands for thickness reduction, weight reduction, power saving and higher definition. For the purpose of uniformly and efficiently guiding incident light to the liquid crystal display side, such planar light source devices are provided with a light guide plate having a uniformly inclined surface on one side and a wedge-shaped cross-section, or a light guide plate having a flat plate shape. Further, the light guide plate may be imparted with a light-scattering function by formation of an irregular pattern on its surface.

The above-described light guide plate can be obtained by injection molding of a thermoplastic resin, and the above-described irregular pattern is provided by transcription of irregularities formed on a surface of an insert. Conventionally, light guide plates are molded from resin materials such as polymethyl methacrylate (PMMA); however, since light guide plates have been recently reduced in thickness in association with reduction in the thickness of displays, the material mechanical strength attained by PMMA is no longer sufficient, and PMMA has thus been gradually replaced with polycarbonate resins having a relatively high mechanical strength.

Conventional polycarbonate resins, however, have a drawback of having lower melt fluidity and notably inferior moldability as compared to PMMA; therefore, studies have been conducted on improvement of the moldability for application of such polycarbonate resins as raw materials of the above-described molded articles.

For example, Patent Document 1 discloses an aromatic polycarbonate resin having a viscosity-average molecular weight of 10,000 to 15,000 as a polycarbonate resin for light guide plate materials, and Patent Document 2 discloses an aromatic polycarbonate resin having a viscosity-average molecular weight of 11,000 to 22,000 as a polycarbonate resin for light guide plate materials. The methods disclosed in these Patent Documents are methods of improving the moldability of a polycarbonate resin by reducing the molecular weight and thereby increasing the melt fluidity of the polycarbonate resin; however, it is needless to say that, usually, the mechanical strength of a polymer material tends to decrease in association with a reduction in the molecular weight. Accordingly, the mechanical strength is reduced in the same manner also in the above-described polycarbonate resins, and these polycarbonate resins neither have a sufficient moldability nor provide a sufficient practical strength as a product.

In this respect, methods of improving the moldability of a conventional bisphenol A-type polycarbonate resin by further adding thereto a novel dihydroxy compound as a monomer have been proposed. For example, Patent Document 3 discloses a polycarbonate resin that is composed of bisphenol A and bisphenol E and has an improved fluidity, and Patent Documents 4 and 5 disclose polycarbonate resins whose fluidity was improved using specific bisphenol compounds. Further, it is also known to add a fluidity modifier such as a plasticizer, or to add a high-fluidity resin such as an oligomer or ABS. However, these polycarbonate resins also have problems in that they cannot withstand the actual use due to their extremely low heat resistance, and that they do not have sufficient fluidity and impact resistance for yielding a light guide plate, and a thin-wall molded article thus cannot be obtained from these polycarbonate resins.

RELATED ART DOCUMENTS

Patent Documents

[Patent Document 1] Japanese Unexamined Patent Application Publication No. 2010-37380
[Patent Document 2] Japanese Unexamined Patent Application Publication No. 2013-139097
[Patent Document 3] Japanese Unexamined Patent Application Publication No. H5-1144
[Patent Document 4] Japanese Unexamined Patent Application Publication No. H6-128371
[Patent Document 5] Japanese Unexamined Patent Application Publication No. S59-131623

SUMMARY OF THE INVENTION

Problems to be Solved by the Invention

In the above-described for light guide plates, a resin material is required to have a fluidity equivalent to that of a common bisphenol A-type polycarbonate resin product having a viscosity-average molecular weight of 10,000 to 15,000 and, in recent years, particularly, a resin material is required to have such a high fluidity that is equivalent to that of a resin product having a viscosity-average molecular weight of 10,000 to 13,000. However, the polycarbonate resins disclosed in Patent Documents 1 to 5 exhibit a notably low impact strength when allowed to have a fluidity in the above-described range and, therefore, have problems in that they not only cannot maintain a product strength but also are cracked in a molding process.

In view of the above-described problems, an object of the present invention to provide an aromatic polycarbonate resin that has not only high fluidity and thin-wall moldability as described above but also excellent hue and transparency.

Means for Solving the Problems

The present inventors intensively studied to discover that an aromatic polycarbonate resin containing a structural unit derived from a specific aromatic dihydroxy compound, a hydrolysate of which aromatic polycarbonate resin contains a certain amount of a specific dihydroxy compound, not only exhibits a high fluidity necessary for molding a thin-wall molded article and a high mechanical strength but also has excellent hue and transparency, thereby completing the present invention.

That is, the gist of the present invention resides in the following [1] to [10].

[1] An aromatic polycarbonate resin, containing a structural unit represented by the following Formula (1), that is derived from an aromatic dihydroxy compound and a carbonate-forming compound, the aromatic polycarbonate resin being characterized in that:

a hydrolysate obtained by hydrolysis of the aromatic polycarbonate resin contains an aromatic dihydroxy compound represented by the following Formula (2) and an aromatic dihydroxy compound represented by the following Formula (3), and the content of the aromatic dihydroxy compound represented by the following Formula (2) in the hydrolysate is 250 ppm by mass or less with respect to that of the aromatic dihydroxy compound represented by the following Formula (3):

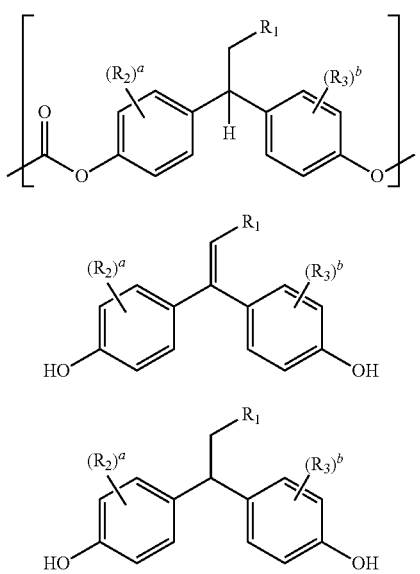

(wherein, $R_1$ represents an alkyl group having 1 to 24 carbon atoms; $R_2$ and $R_3$ each independently represent a monovalent hydrocarbon group having 1 to 15 carbon atoms; and a and b each independently represent an integer of 0 to 4).

[2] The aromatic polycarbonate resin according to [1], having a viscosity-average molecular weight of 9,000 or higher.

[3] The aromatic polycarbonate resin according to [1] or [2], wherein the content of the aromatic dihydroxy compound represented by Formula (2) in the hydrolysate is not less than 1 ppm by mass with respect to that of the aromatic dihydroxy compound represented by Formula (3).

[4] The aromatic polycarbonate resin according to any one of [1] to [3], wherein, in Formulae (1) to (3), $R_1$ represents an alkyl group having 6 to 24 carbon atoms.

[5] A method of producing the aromatic polycarbonate resin according to any one of [1] to [4], the method including the polymerization step of polymerizing the aromatic dihydroxy compound and the carbonate-forming compound in the presence of an alkali catalyst.

[6] The method of producing the aromatic polycarbonate resin according to [5], wherein the polymerization step is performed by a transesterification method.

[7] The method of producing the aromatic polycarbonate resin according to [6], wherein, in the polymerization step, a transesterification catalyst is deactivated after a transesterification reaction, without substantial solidification of the resulting aromatic polycarbonate resin.

[8] The method of producing the aromatic polycarbonate resin according to [7], wherein, in the polymerization step, a deactivator is added in an amount of not less than 3 equivalents and 50 equivalents or less with respect to the transesterification catalyst.

[9] An aromatic dihydroxy compound, containing aromatic dihydroxy compounds represented by the following Formulae (2) and (3), wherein the content of the aromatic dihydroxy compound represented by Formula (2) is 250 ppm by mass or less:

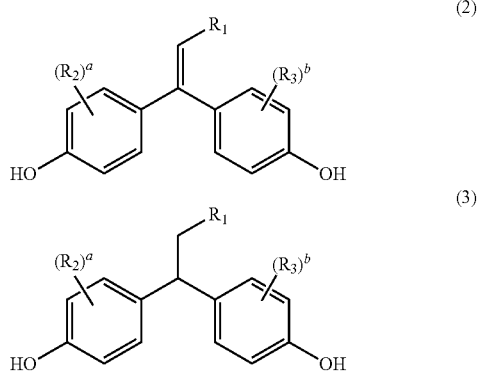

(wherein, $R_1$ represents an alkyl group having 1 to 24 carbon atoms; $R_2$ and $R_3$ each independently represent a monovalent hydrocarbon group having 1 to 15 carbon atoms; and a and b each independently represent an integer of 0 to 4).

[10] The aromatic dihydroxy compound according to [9], wherein the content of the aromatic dihydroxy compound represented by Formula (2) is not less than 1 ppm by mass.

[11] The aromatic dihydroxy compound according to [9] or [10], wherein, in Formulae (2) and (3), $R_1$ represents an alkyl group having 6 to 24 carbon atoms.

[12] An aromatic polycarbonate resin composition, containing the aromatic polycarbonate resin according to any one of [1] to [4], the aromatic polycarbonate resin composition being characterized by further containing an aromatic polycarbonate resin composed of carbonate structural units derived from 2,2-bis(4-hydroxyphenyl)propane.

[13] A method of producing an aromatic polycarbonate resin containing a structural unit represented by the following Formula (1), the method including the step of polymerizing an aromatic dihydroxy compound and a carbonate-forming compound such that a hydrolysate obtained by hydrolysis of the aromatic polycarbonate resin contains an aromatic dihydroxy compound represented by the following Formula (2) and an aromatic dihydroxy compound represented by the following Formula (3), and that the content of the aromatic dihydroxy compound represented by the following Formula (2) in the hydrolysate is 250 ppm by mass or less with respect to that of the aromatic dihydroxy compound represented by the following Formula (3):

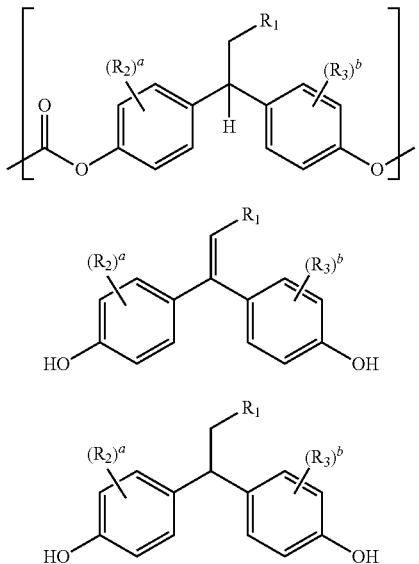

(wherein, $R_1$ represents an alkyl group having 1 to 24 carbon atoms; $R_2$ and $R_3$ each independently represent a monovalent hydrocarbon group having 1 to 15 carbon atoms; and a and b each independently represent an integer of 0 to 4).

Effects of the Invention

According to the aromatic polycarbonate resin of the present invention, an aromatic polycarbonate resin material having excellent thin-wall moldability and impact strength as well as excellent hue and transparency can be provided. This aromatic polycarbonate resin is extremely valuable in terms of industrial applicability since it can yield a molded article having excellent strength as well as excellent hue and transparency with high productivity even in those cases where a large-sized molded article such as a resin glass window, or a thin-wall molded article such as a light guide plate, is to be obtained.

MODES FOR CARRYING OUT THE INVENTION

The present invention will now be described in detail referring to embodiments, examples and the like thereof; however, the present invention should not be interpreted as being limited to the embodiments, examples and the like described below.

In the present specification, unless otherwise specified, those numerical ranges expressed with "to" each denote a range that includes the numerical values stated before and after "to" as the lower and upper limit values, respectively. Further, unless otherwise specified, "part(s)" means part (s) by mass, representing an amount based on mass.

Aromatic Polycarbonate Resin

The aromatic polycarbonate resin of the present invention is characterized by containing a carbonate structural unit represented by the following Formula (1):

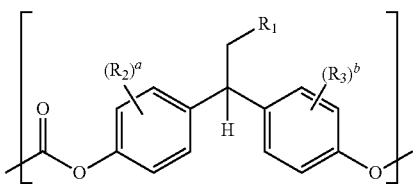

In Formula (1), $R_1$ represents an alkyl group having 1 to 24 carbon atoms; $R_2$ and $R_3$ each independently represent a monovalent hydrocarbon group having 1 to 15 carbon atoms; and a and b each independently represent an integer of 0 to 4.

By having such a specific carbonate structure, the aromatic polycarbonate resin of the present invention exhibits a notably favorable balance between fluidity and strength, such as impact strength, bending strength, and cyclic fatigue strength.

In the aromatic polycarbonate resin of the present invention, the fluidity in melting is improved as the number of the carbon atoms of $R_1$ in the above-described carbonate structural unit increases. This is because the presence of such an alkyl chain in this structure moderately inhibits entanglement of polymer chains in melting to reduce friction between the polymer chains, whereby a high fluidity can be expressed.

A high fluidity is expressed when the alkyl chain is further extended; however, a further extension of the alkyl chain is not preferred since it markedly reduces the heat resistance and the mechanical strength, and the transparency of the aromatic polycarbonate resin of the present invention may be impaired due to an increase in the crystallinity of long aliphatic chain. Therefore, the number of the carbon atoms of $R_1$ in the carbonate structural unit is preferably 1 to 24, more preferably 6 to 24, still more preferably 6 to 18.

Examples of the alkyl group having 1 to 24 carbon atoms include linear or branched alkyl groups, and alkyl groups partially having a cyclic structure. Thereamong, for an effective fluidity improvement of the aromatic polycarbonate resin of the present invention, the alkyl group having 1 to 24 carbon atoms is preferably a linear or branched alkyl group.

Specific examples of the linear alkyl groups include a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, an n-icosyl group, an n-henicosyl group, an n-docosyl group, an n-tricosyl group, and an n-tetracosyl group, among which an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, and n-nonadecyl group are preferred. By the presence of such an alkyl group, the fluidity and the impact resistance of the aromatic polycarbonate resin of the present invention can be improved more effectively.

Specific examples of the branched alkyl groups include a methylpropyl group, a methylbutyl group, a methylpentyl group, a methylhexyl group, a methylheptyl group, a methyloctyl group, a methylnonyl group, a methyldecyl group, a methylundecyl group, a methyldodecyl group, a methyltridecyl group, a methyltetradecyl group, a methylpentadecyl group, a methylhexadecyl group, a methylheptadecyl group, a methyloctadecyl group, a methylnonadecyl group, a methylicosyl group, a methylicosyl group, a methylhenicosyl group, a methyldocosyl group, a methyltricosyl group, a dimethylpropyl group, a dimethylbutyl group, a dimethylpentyl group, a dimethylhexyl group, a dimethylheptyl group, a dimethyloctyl group, a dimethylnonyl group, a dimethyldecyl group, a dimethylundecyl group, a dimethyldodecyl group, a dimethyltridecyl group, a dimethyltetradecyl group, a dimethylpentadecyl group, a dimethylhexadecyl group, a dimethylheptadecyl group, a dimethyloctadecyl group, a dimethylnonadecyl group, a dimethylicosyl group, a dimethylicosyl group, a dimethylhenicosyl group, a dimethyldocosyl group, a trimethylbutyl group, a trimethylpentyl group, a trimethylhexyl group, a trimethylheptyl group, a trimethyloctyl group, a trimethylnonyl group, a trimethyldecyl group, a trimethylundecyl group, a trimethyldodecyl group, a trimethyltridecyl group, a trimethyltetradecyl group, a trimethylpentadecyl group, a trimethylhexadecyl group, a trimethylheptadecyl group, a trimethyloctadecyl group, a trimethylnonadecyl group, a trimethylicosyl group, a trimethylicosyl group, a trimethylhenicosyl group, an ethylpentyl group, an ethylhexyl group, an ethylheptyl group, an ethyloctyl group, an ethylnonyl group, an ethyldecyl group, an ethylundecyl group, an ethyldodecyl group, an ethyltridecyl group, an ethyltetradecyl group, an ethylpentadecyl group, an ethylhexadecyl group, an ethylheptadecyl group, an ethyloctadecyl group, an ethylnonadecyl group, an ethylicosyl group, an ethylicosyl group, an ethylhenicosyl group, an ethyldocosyl group, a butylpropylhexyl group, a propylheptyl group, a propyloctyl group, a propylnonyl group, a propyldecyl group, a propylundecyl group, a propyldodecyl group, a propyltridecyl group, a propyltetradecyl group, a propylpentadecyl group, a propylhexadecyl group, a propylheptadecyl group, a propyloctadecyl group, a propylnonadecyl group, a propylicosyl group, a propylicosyl group, a propylhenicosyl group, a butylhexyl group, a butylheptyl group, a butyloctyl group, a butylnonyl group, a butyldecyl group, a butylundecyl group, a butyldodecylgroup, a butyltridecyl group, a butyltetradecyl group, a butylpentadecyl group, a butylhexadecyl group, a butylheptadecyl group, a butyloctadecyl group, a butylnonadecyl group, a butylicosyl group, and a butylicosyl group.

It is noted here that, in the above-exemplified branched alkyl groups, the positions of branches are arbitrary.

In the carbonate structural unit, $R_2$ and $R_3$ each represent a monovalent hydrocarbon group having 1 to 15 carbon atoms. By the presence of the monovalent hydrocarbon group having 1 to 15 carbon atoms, the fluidity, the strength, the hardness, the chemical resistance and the like of the aromatic polycarbonate resin of the present invention can be improved. Examples of the monovalent hydrocarbon group having 1 to 15 carbon atoms include alkyl groups having 1 to 15 carbon atoms and alkenyl groups having 2 to 15 carbon atoms, and these groups may be linear, branched or cyclic. Examples of such monovalent hydrocarbon groups include a methyl group, an ethyl group, a propyl group, an isopropyl group, an n-butyl group, an isobutyl group, a sec-butyl group, a Cert-butyl group, a pentyl group, an n-hexyl group, cyclohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, a phenyl group, and a tolyl group, among which a methyl group is preferred.

Further, in the carbonate structural unit, a and b each independently represent an integer of 0 to 4, preferably an integer of 0 to 2, more preferably an integer of 0 to 1, still more preferably 0.

The aromatic polycarbonate resin of the present invention may be a copolymer constituted only by the carbonate structural unit represented by Formula (1), or a copolymer containing one or more kinds of carbonate structural units that are each derived from other dihydroxy compound and different from the above-described carbonate structural unit. Further, the form of the copolymer can be selected from various forms of copolymers, including random copolymers and block copolymers.

In the aromatic polycarbonate resin, the carbonate structural unit represented by Formula (1) is contained in an amount of preferably not less than 1% by mole, more preferably not less than 2.5% by mole, still more preferably not less than 4% by mole. The upper limit of the amount may be 49% by mole or less, or 36.5% by mole or less.

Flow Value of Aromatic Polycarbonate Resin (Q Value)

The aromatic polycarbonate resin of the present invention preferably has a flow value (Q value) of 6 or higher (unit: $10^{-2}$ cm$^3$/sec) as measured in accordance with Appendix C of JIS K7210 (1999) using a Koka-type flow tester under the conditions of 240° C. and 160 kgf/cm$^2$. The Q value, which is an index of the melt viscosity, is different from MVR (melt volume rate) and MFR (melt flow rate) in that it represents the melt viscosity in a high-shear-rate range that resembles the actual condition of injection molding. A higher Q value indicates a higher fluidity and a superior moldability. For molding a thin-wall molded article such as the above-described light guide plate, the Q value is preferably 10 or higher, more preferably 15 or higher, still more preferably 20 or higher, particularly preferably 25 or higher. Meanwhile, the upper limit of the Q value is not particularly restricted as long as excellent physical properties of the aromatic polycarbonate resin of the present invention are not deteriorated; however, it is usually 80 or less, preferably 70 or less, more preferably 60 or less, still more preferably 50 or less, particularly preferably 45 or less.

When controlling the Q value of the aromatic polycarbonate resin of the present invention to be in the above-described range, two or more kinds of aromatic polycarbonate resins having different Q values may be mixed and, in this case, the Q value of the aromatic polycarbonate resin of the present invention may be controlled by mixing an aromatic polycarbonate resin having a Q value outside the above-described preferred range.

Molecular Weight of Aromatic Polycarbonate Resin

The molecular weight of the aromatic polycarbonate resin of the present invention is not particularly restricted; however, it is usually 9,000 or higher and 24,000 or less in terms of viscosity-average molecular weight (Mv) calculated from the solution viscosity. When the viscosity-average molecular weight is less than the above-described lower limit value, the strength of the aromatic polycarbonate resin of the present invention tends to be insufficient, whereas when the viscosity-average molecular weight is higher than the above-described upper limit value, the fluidity tends to be insufficient, which is not preferred. From this standpoint, the viscosity-average molecular weight (Mv) of the aromatic polycarbonate resin of the present invention is preferably 10,000 or higher, more preferably 11,000 or higher, still more preferably 11,500 or higher, but preferably 17,500 or less, more preferably 16,000 or less, still more preferably 15,000 or less.

The viscosity-average molecular weight (Mv) of the aromatic polycarbonate resin of the present invention means a value determined by measuring the intrinsic viscosity (limiting viscosity) [η] (unit: dL/g) at a temperature of 20° C. using an Ubbelohde viscometer with methylene chloride as a solvent, and applying the measured value to the Schnell's viscosity equation, namely $\eta = 1.23 \times 10^{-4} \, Mv^{0.83}$. The intrinsic viscosity (limiting viscosity) [η] is a value determined by measuring the specific viscosity [ηsp] at each solution concentration [C] (g/dL) and applying the measured value to the following equation:

$$\eta = \lim_{c \to 0} \eta_{sp}/c$$

The intrinsic viscosity (dL/g) of the aromatic polycarbonate resin of the present invention is not particularly restricted and correlates with the above-described viscosity-average molecular weight; however, it is usually 0.24 to 0.54, preferably 0.26 or higher, more preferably 0.28 or higher, still more preferably 0.29 or higher, but preferably 0.42 or lower, more preferably 0.39 or lower, still more preferably 0.37 or lower.

Amount of Terminal Hydroxyl Groups in Aromatic Polycarbonate Resin

The amount of terminal hydroxyl groups in the aromatic polycarbonate resin of the present invention is not particularly restricted as long as excellent physical properties of the aromatic polycarbonate resin of the present invention are not deteriorated; however, it is usually 10 to 2,000 ppm by mass. The amount of terminal hydroxyl groups in the aromatic polycarbonate resin of the present invention is preferably not less than 20 ppm by mass, more preferably not less than 50 ppm by mass, still more preferably not less than 100 ppm by mass, but preferably 1,700 ppm by mass or less, more preferably 1,500 ppm by mass or less, still more preferably 1,200 ppm by mass or less. When the amount of terminal hydroxyl groups is the lower limit value of this range or greater, the hue and the productivity of the aromatic polycarbonate resin and the aromatic polycarbonate resin composition of the present invention can be further improved, while when the amount of terminal hydroxyl groups is the upper limit value of the above-described range or less, the thermal stability and the moist-heat stability of the aromatic polycarbonate resin and the aromatic polycarbonate resin composition of the present invention can be further improved.

The amount of terminal hydroxyl groups in the aromatic polycarbonate resin of the present invention can be adjusted to be in the above-described range by any known method. For example, in a case of producing the aromatic polycarbonate resin of the present invention by polycondensation based on transesterification reaction, the amount of terminal hydroxyl groups can be adjusted to be in the above-described range by adjusting the mixing ratio of the carbonate-forming compound and the aromatic dihydroxy compound, the degree of pressure reduction during the transesterification reaction, and/or the like.

Examples of a more active adjustment method include a method of separately mixing a chain terminator during the reaction. Examples of the chain terminator used in this method include monohydric phenols, monobasic carboxylic acids, and diester carbonates. These chain terminators may be used singly, or two or more thereof may be used in any combination at any ratio.

Meanwhile, in a case of producing the aromatic polycarbonate resin of the present invention by an interfacial polymerization method, the amount of terminal hydroxyl groups can be arbitrarily adjusted by adjusting the amount of a molecular weight modifier (chain terminator) to be incorporated.

As for the unit of the amount of terminal hydroxyl groups, the mass of terminal hydroxyl groups with respect to the mass of the aromatic polycarbonate resin is indicated in ppm. As a method of measuring the amount of terminal hydroxyl groups, colorimetry based on a titanium tetrachloride/acetic acid method (the method described in Macromol. Chem. 88, 215 (1965)) is employed. In an aromatic polycarbonate resin copolymer composed of plural dihydroxy compounds, samples are prepared for at least three levels of concentration by mixing the corresponding dihydroxy compounds in accordance with a copolymerization ratio, and a calibration curve is subsequently generated from the data obtained at the three or more points, after which the amount of terminal hydroxyl groups in the aromatic polycarbonate resin copolymer is measured. The detection wavelength is set at 546 nm.

Amounts of Compounds of Formulae (2) and (3) in Hydrolysate of Aromatic Polycarbonate Resin A hydrolysate obtained by hydrolysis of the aromatic polycarbonate resin of the present invention contains an aromatic dihydroxy compound represented by the following Formula (2) and an aromatic dihydroxy compound represented by the following Formula (3). Further, in the hydrolysate, the content of the aromatic dihydroxy compound represented by the following Formula (2) is 250 ppm by mass or less with respect to the aromatic dihydroxy compound represented by the following Formula (3). When this value exceeds 250 ppm by mass, the hue of the resin is deteriorated, making the resin unsuitable for an optical material such as a light guide plate. These specific structures are analyzed by the below-described analysis method (1).

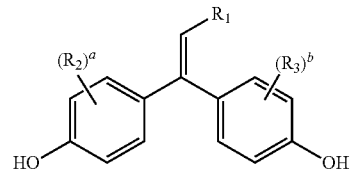

(2)

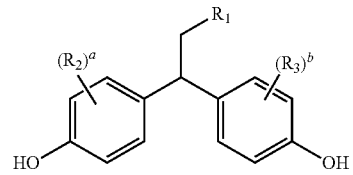

(3)

Analysis method (1): First, 0.5 g of a sample is dissolved in 5 mL of dicyclomethane (reagent grade, manufactured by Wako Pure Chemical Industries, Ltd.). Then, 45 mL of methanol (reagent grade, manufactured by Kishida Chemical Co., Ltd.) is added, followed by a further addition of 5 mL of a 25% aqueous sodium hydroxide solution (manufactured by Wako Pure Chemical Industries, Ltd.). The resulting mixture is heated to reflux with stirring at 75° C. for 30 minutes. This mixture is cooled and, after subsequently adding thereto 7 mL of 17.5% hydrochloric acid, the volume of the resultant is adjusted to be 100 mL with methanol and pure water. The thus prepared solution is measured by high-performance liquid chromatography under the following conditions.

Detector: SPD-10AVp, manufactured by Shimadzu Corporation

Analysis column: YMC-Pack ODS-AM12S03-L546WT (particle size: 3 μm, pore size: 12 nm, inner diameter: 4.6 mm, length: 75 mm)

Mobile phase: (A) 0.1% aqueous trifluoroacetic acid solution, (B) methanol for high-performance liquid chromatography (manufactured by Kishida Chemical Co., Ltd.)

Mobile phase flow rate: 1.0 mL/min

Sample injection amount: 20 μL

Gradient condition: continuous change in concentration from 60% mobile phase (A) and 40% mobile phase (B) to 5% mobile phase (A) to 95% mobile phase (B) in 25 minutes.

Column temperature: 40° C.

Detector wavelength: 280 nm

The content of the aromatic dihydroxy compound represented by Formula (2) in the hydrolysate is preferably 250 ppm by mass or less, more preferably 100 ppm by mass or less, still more preferably 60 ppm by mass or less, with respect to that of the aromatic dihydroxy compound represented by Formula (3). Meanwhile, the lower limit value of the content is usually larger than 0 ppm by mass, preferably 1 ppm by mass or larger, more preferably 3 ppm by mass or larger.

The content of the aromatic dihydroxy compound represented by Formula (2) in the hydrolysate can be controlled in the above-described range by, for example, appropriately adjusting the catalyst species and amount, the temperature conditions, the humidity conditions, the pressure conditions, the retention time in each polymerization vessel, the air tightness of the equipment, the air flow conditions and the like in the production process.

Identification of Compounds of Formulae (2) and (3) in Aromatic Polycarbonate Resin Hydrolysate During an analysis conducted by the above-described analysis method, an analysis liquid is fractionated when a peak derived from a specific structure is detected. Subsequently, methanol is removed therefrom by distillation using an evaporator, and the component of interest is extracted with an addition of methylene chloride. Thereafter, the resulting methylene chloride phase is evaporated to dryness, whereby a high-purity specific component is obtained. For the thus obtained specific component, its structure is identified by performing $^1$H-NMR, H-H COSY, HMQC and HMBC measurements. Further, whether or not the identified structure is correct can be confirmed by an LC-MS analysis.

Under the above-described conditions, a structure of Formula (3) in which $R_1$ has 11 carbon atoms and a and b represent 0, and a structure of Formula (2) in which $R_1$ has 11 carbon atoms and a and b represent 0 are detected at 22.35 minutes and 22.06 minutes, respectively, although there may be some errors depending on the state of column deterioration and the timing of the production.

Hue of Aromatic Polycarbonate Resin

The present invention provides an aromatic polycarbonate resin having excellent hue. The hue of the aromatic polycarbonate resin is usually 5 or less, preferably 3 or less, in terms of yellow index value (YI value). The upper limit thereof is not restricted; however, it is usually −0.3 or higher.

The YI value can be reduced by controlling the amount of the compound represented by Formula (2) in the hydrolysate of the aromatic polycarbonate resin to be a moderate value.

The hue can be evaluated by measuring the YI value (yellow index value) of light reflected from a pellet in accordance with ASTM P1925. Specifically, a spectrophotometric colorimeter CM-5 manufactured by Konica Minolta, Inc. is used as an apparatus, and a measurement diameter of 30 mm and SCE are selected as measurement conditions. A calibration glass for petri dish measurement, CM-A212, is fitted to the measuring part, and a zero calibration box CM-A124 is placed thereon to perform zero calibration, after which white calibration is performed using the built-in white calibration plate.

A measurement is performed using a white calibration plate CM-A210 to confirm that the values of L*, a*, b* and YI are 99.40±0.05, 0.03±0.01, −0.43±0.01 and −0.58±0.01, respectively. The measurement of the pellet is performed by filling a cylindrical glass container having an inner diameter of 30 mm and a height of 50 mm with the pellet to a depth of about 40 mm. An operation of taking out the pellet from the glass container and performing the measurement again is repeated twice, and an average value of three measurements in total is used. A smaller YI value means that the resin has superior color tone with less yellowness.

Method of Producing Aromatic Polycarbonate Resin

The aromatic polycarbonate resin of the present invention is obtained by polycondensation of dihydroxy compounds, which include at least one aromatic dihydroxy compound necessary for forming the carbonate structural unit represented by Formula (1) and other aromatic dihydroxy compound that is optionally selected, with a carbonate-forming compound.

The aromatic dihydroxy compound necessary for forming the carbonate structural unit represented by Formula (1) is, for example, an aromatic dihydroxy compound containing those represented by the following Formulae (2) and (3):

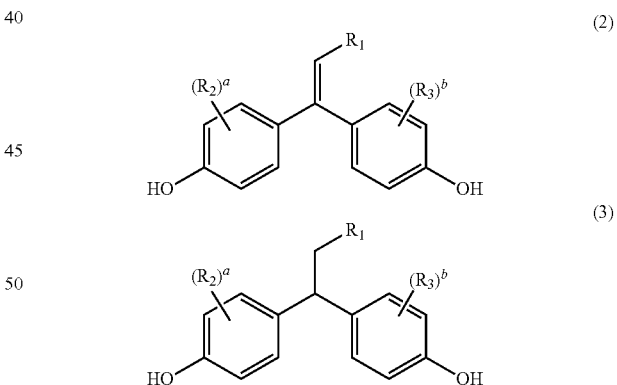

In Formulae (2) and (3), the definitions and preferred examples of $R_1$, $R_2$, $R_3$, a, and b are the same as those described above for Formula (1).

In the aromatic dihydroxy compound used for forming the carbonate structural unit represented by Formula (1), a compound represented by Formula (3) is a main component, and an aromatic dihydroxy compound represented by Formula (2) is contained in a small amount. Specifically, the content of the aromatic dihydroxy compound represented by Formula (2) is preferably 250 ppm by mass or less, more preferably 100 ppm by mass or less, still more preferably 60 ppm by mass or less. Meanwhile, the lower limit value thereof is usually larger than 0 ppm by mass, preferably 1 ppm by mass or larger, more preferably 3 ppm by mass or larger.

As described above, a compound represented by Formula (3) is the main component in the aromatic dihydroxy compound containing those represented by Formulae (2) and (3); however, the aromatic dihydroxy compound may also contain polyhydric phenol compounds represented by the following Formulae (4) and (5). It is noted here that the term "main component" used herein means a component with the largest amount among the components that are contained, and the content of the main component is specifically not less than 50% by mass and may be not less than 80% by mass, not less than 90% by mass, not less than 95% by mass, not less than 98% by mass, not less than 99% by mass, or not less than 99.9% by mass.

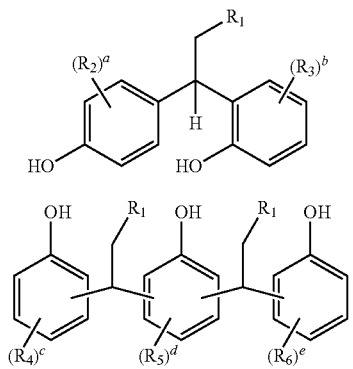

In Formulae (4) and (5), the definitions and preferred examples of $R_1$, $R_2$, $R_3$, a, and b are the same as those described above for Formula (1); $R_4$, $R_5$, and $R_6$ each independently represent a monovalent hydrocarbon group having 1 to 15 carbon atoms; and c, d, and e each independently represent an integer of 0 to 4.

Specific examples of the aromatic dihydroxy compound necessary for forming the carbonate structural unit represented by Formula (1) include the followings:
1,1-bis(4-hydroxyphenyl)octane,
1,1-bis(2-hydroxyphenyl)octane,
1-(2-hydroxyphenyl)-1-(4-hydroxyphenyl)octane,
1,1-bis(4-hydroxyphenyl)nonane,
1,1-bis(2-hydroxyphenyl)nonane,
1-(2-hydroxyphenyl)-1-(4-hydroxyphenyl)nonane,
1,1-bis(4-hydroxyphenyl)decane,
1,1-bis(2-hydroxyphenyl)decane,
1-(2-hydroxyphenyl)-1-(4-hydroxyphenyl)decane,
1,1-bis(4-hydroxyphenyl)undecane,
1,1-bis(2-hydroxyphenyl)undecane,
1-(2-hydroxyphenyl)-1-(4-hydroxyphenyl)undecane,
1,1-bis(4-hydroxyphenyl)dodecane,
1,1-bis(2-hydroxyphenyl)dodecane,
1-(2-hydroxyphenyl)-1-(4-hydroxyphenyl)dodecane,
1,1-bis(4-hydroxyphenyl)tridecane,
1,1-bis(2-hydroxyphenyl)tridecane,
1-(2-hydroxyphenyl)-1-(4-hydroxyphenyl)tridecane,
1,1-bis(4-hydroxyphenyl)tetradecane,
1,1-bis(2-hydroxyphenyl)tetradecane,
1-(2-hydroxyphenyl)-1-(4-hydroxyphenyl)tetradecane,
1,1-bis(4-hydroxyphenyl)pentadecane,
1,1-bis(2-hydroxyphenyl)pentadecane,
1-(2-hydroxyphenyl)-1-(4-hydroxyphenyl)pentadecane,
1,1-bis(4-hydroxyphenyl)hexadecane,
1,1-bis(2-hydroxyphenyl)hexadecane,
1-(2-hydroxyphenyl)-1-(4-hydroxyphenyl)hexadecane,
1,1-bis(4-hydroxyphenyl)heptadecane,
1,1-bis(2-hydroxyphenyl)heptadecane,
1-(2-hydroxyphenyl)-1-(4-hydroxyphenyl)heptadecane,
1,1-bis(4-hydroxyphenyl)octadecane,
1,1-bis(2-hydroxyphenyl)octadecane,
1-(2-hydroxyphenyl)-1-(4-hydroxyphenyl)octadecane,
1,1-bis(4-hydroxyphenyl)nonadecane,
1,1-bis(2-hydroxyphenyl)nonadecane,
1-(2-hydroxyphenyl)-1-(4-hydroxyphenyl)nonadecane,
1,1-bis(4-hydroxyphenyl)icosane,
1,1-bis(2-hydroxyphenyl)icosane,
1-(2-hydroxyphenyl)-1-(4-hydroxyphenyl)icosane,
1,1-bis(4-hydroxyphenyl)henicosane,
1,1-bis(2-hydroxyphenyl)henicosane,
1-(2-hydroxyphenyl)-1-(4-hydroxyphenyl)henicosane,
1,1-bis(4-hydroxyphenyl)docosane,
1,1-bis(2-hydroxyphenyl)docosane,
1-(2-hydroxyphenyl)-1-(4-hydroxyphenyl)docosane,
1,1-bis(4-hydroxyphenyl)tricosane,
1,1-bis(2-hydroxyphenyl)tricosane,
1-(2-hydroxyphenyl)-1-(4-hydroxyphenyl)tricosane,
1,1-bis(4-hydroxyphenyl)tetracosane,
1,1-bis(2-hydroxyphenyl)tetracosane,
1-(2-hydroxyphenyl)-1-(4-hydroxyphenyl)tetracosane,
1,1-bis(3-methyl-4-hydroxyphenyl)octane,
1,1-bis(2-hydroxy-3-methylphenyl)octane,
1-(2-hydroxy-3-methyl-phenyl)-1-(3-methyl-4-hydroxyphenyl)octane,
1,1-bis(3-methyl-4-hydroxyphenyl)nonane,
1,1-bis(2-hydroxy-3-methylphenyl)nonane,
1-(2-hydroxy-3-methyl-phenyl)-1-(3-methyl-4-hydroxyphenyl)nonane,
1,1-bis(3-methyl-4-hydroxyphenyl)decane,
1,1-bis(2-hydroxy-3-methylphenyl)decane,
1-(2-hydroxy-3-methyl-phenyl)-1-(3-methyl-4-hydroxyphenyl)decane,
1,1-bis(3-methyl-4-hydroxyphenyl)undecane,
1,1-bis(2-hydroxy-3-methylphenyl)undecane,
1-(2-hydroxy-3-methyl-phenyl)-1-(3-methyl-4-hydroxyphenyl)undecane,
1,1-bis(3-methyl-4-hydroxyphenyl)dodecane,
1,1-bis(2-hydroxy-3-methylphenyl)dodecane,
1-(2-hydroxy-3-methyl-phenyl)-1-(3-methyl-4-hydroxyphenyl)dodecane,
1,1-bis(3-methyl-4-hydroxyphenyl)tridecane,
1,1-bis(2-hydroxy-3-methylphenyl)tridecane,
1-(2-hydroxy-3-methyl-phenyl)-1-(3-methyl-4-hydroxyphenyl)tridecane,
1,1-bis(3-methyl-4-hydroxyphenyl)tetradecane,
1,1-bis(2-hydroxy-3-methylphenyl)tetradecane,
1-(2-hydroxy-3-methyl-phenyl)-1-(3-methyl-4-hydroxyphenyl)tetradecane,
1,1-bis(3-methyl-4-hydroxyphenyl)pentadecane,
1,1-bis(2-hydroxy-3-methylphenyl)pentadecane,
1-(2-hydroxy-3-methyl-phenyl)-1-(3-methyl-4-hydroxyphenyl)pentadecane,
1,1-bis(3-methyl-4-hydroxyphenyl)hexadecane,
1,1-bis(2-hydroxy-3-methylphenyl)hexadecane,
1-(2-hydroxy-3-methyl-phenyl)-1-(3-methyl-4-hydroxyphenyl)hexadecane,
1,1-bis(3-methyl-4-hydroxyphenyl)heptadecane,
1,1-bis(2-hydroxy-3-methylphenyl)heptadecane,
1-(2-hydroxy-3-methyl-phenyl)-1-(3-methyl-4-hydroxyphenyl)heptadecane, 1,1-bis(3-methyl-4-hydroxyphenyl)octadecane,
1,1-bis(2-hydroxy-3-methylphenyl)octadecane,
1-(2-hydroxy-3-methyl-phenyl)-1-(3-methyl-4-hydroxyphenyl)octadecane,
1,1-bis(3-methyl-4-hydroxyphenyl)nonadecane,
1,1-bis(2-hydroxy-3-methylphenyl)nonadecane,
1-(2-hydroxy-3-methyl-phenyl)-1-(3-methyl-4-hydroxyphenyl)nonadecane,
1,1-bis(3-methyl-4-hydroxyphenyl)icosane,
1,1-bis(2-hydroxy-3-methylphenyl)icosane,
1-(2-hydroxy-3-methyl-phenyl)-1-(3-methyl-4-hydroxyphenyl)icosane,
1,1-bis(3-methyl-4-hydroxyphenyl)henicosane,
1,1-bis(2-hydroxy-3-methylphenyl)henicosane,
1-(2-hydroxy-3-methyl-phenyl)-1-(3-methyl-4-hydroxyphenyl)henicosane,
1,1-bis(3-methyl-4-hydroxyphenyl)docosane,
1,1-bis(2-hydroxy-3-methylphenyl)docosane,
1-(2-hydroxy-3-methyl-phenyl)-1-(3-methyl-4-hydroxyphenyl)docosane,
1,1-bis(3-methyl-4-hydroxyphenyl)tricosane,
1,1-bis(2-hydroxy-3-methylphenyl)tricosane,
1-(2-hydroxy-3-methyl-phenyl)-1-(3-methyl-4-hydroxyphenyl)tricosane,
1,1-bis(3-methyl-4-hydroxyphenyl)tetracosane,
1,1-bis(2-hydroxy-3-methylphenyl)tetracosane,
1-(2-hydroxy-3-methyl-phenyl)-1-(3-methyl-4-hydroxyphenyl)tetracosane,
1,1-bis(3,5-dimethyl-4-hydroxyphenyl)octane,
1,1-bis(3,5-dimethyl-4-hydroxyphenyl)nonane,
1,1-bis(3,5-dimethyl-4-hydroxyphenyl)decane,
1,1-bis(3,5-dimethyl-4-hydroxyphenyl)undecane,
1,1-bis(3,5-dimethyl-4-hydroxyphenyl)dodecane,
1,1-bis(3,5-dimethyl-4-hydroxyphenyl)tridecane,
1,1-bis(3,5-dimethyl-4-hydroxyphenyl)tetradecane,
1,1-bis(3-ethyl-4-hydroxyphenyl)nonane,
1,1-bis(3-ethyl-4-hydroxyphenyl)decane,
1,1-bis(3-ethyl-4-hydroxyphenyl)undecane,
1,1-bis(3-ethyl-4-hydroxyphenyl)dodecane,
1,1-bis(3-propyl-4-hydroxyphenyl)nonane,
1,1-bis(3-propyl-4-hydroxyphenyl)decane,
1,1-bis(3-propyl-4-hydroxyphenyl)undecane,
1,1-bis(3-propyl-4-hydroxyphenyl)dodecane,
1,1-bis(3-butyl-4-hydroxyphenyl)nonane,
1,1-bis(3-butyl-4-hydroxyphenyl)decane,
1,1-bis(3-butyl-4-hydroxyphenyl)undecane,
1,1-bis(3-butyl-4-hydroxyphenyl)dodecane,
1,1-bis(3-nonyl-4-hydroxyphenyl)nonane,
1,1-bis(3-nonyl-4-hydroxyphenyl)decane,
1,1-bis(3-nonyl-4-hydroxyphenyl)undecane, and
1,1-bis(3-nonyl-4-hydroxyphenyl)dodecane.

Among these aromatic dihydroxy compounds, from the standpoint of thermal stability, hue and impact strength, the aromatic dihydroxy compound necessary for forming the carbonate structural unit represented by Formula (1) is particularly preferably:
1,1-bis(4-hydroxyphenyl)octane,
1,1-bis(4-hydroxyphenyl)nonane,
1,1-bis(4-hydroxyphenyl)decane,
1,1-bis(4-hydroxyphenyl)undecane,
1,1-bis(4-hydroxyphenyl)dodecane,
1,1-bis(4-hydroxyphenyl)tridecane,
1,1-bis(4-hydroxyphenyl)tetradecane,
1,1-bis(4-hydroxyphenyl)pentadecane,
1,1-bis(4-hydroxyphenyl)hexadecane,
1,1-bis(4-hydroxyphenyl)heptadecane,
1,1-bis(4-hydroxyphenyl)octadecane, or
1,1-bis(4-hydroxyphenyl)nonadecane.

The other dihydroxy compound used for forming the carbonate structural unit represented by Formula (1) is not particularly restricted, and may be an aromatic dihydroxy compound having an aromatic ring in the molecular skeleton, or an aliphatic dihydroxy compound having no aromatic ring. Further, the other dihydroxy compound may be a dihydroxy compound into which a hetero atom, such as N (nitrogen), S (sulfur), P (phosphorus) or Si (silicon), and/or a hetero-bond is/are introduced for imparting various physical properties.

From the standpoint of heat resistance, thermal stability and strength, an aromatic dihydroxy compound is preferably used as the other dihydroxy compound. Specific examples of the aromatic dihydroxy compound include the followings:
dihydroxybenzenes, such as 1,2-dihydroxybenzene, 1,3-dihydroxybenzene (i.e. resorcinol), and 1,4-dihydroxybenzene;
dihydroxybiphenyls, such as 2,5-dihydroxybiphenyl, 2,2'-dihydroxybiphenyl, and 4,4'-dihydroxybiphenyl;
dihydroxynaphthalenes, such as 2,2'-dihydroxy-1,1'-binaphthyl, 1,2-dihydroxynaphthalene, 1,3-dihydroxynaphthalene, 2,3-dihydroxynaphthalene, 1,6-dihydroxynaphthalene, 2,6-dihydroxynaphthalene, 1,7-dihydroxynaphthalene, and 2,7-dihydroxynaphthalene;
dihydroxydiaryl ethers, such as 2,2'-dihydroxydiphenyl ether, 3,3'-dihydroxydiphenyl ether, 4,4'-dihydroxydiphenyl ether, 4,4'-dihydroxy-3,3'-dimethyldiphenyl ether, 1,4-bis(3-hydroxyphenoxy)benzene, and 1,3-bis(4-hydroxyphenoxy)benzene;
bis(hydroxyaryl)alkanes, such as
1,1-bis(4-hydroxyphenyl)propane,
2,2-bis(3-methyl-4-hydroxyphenyl)propane,
2,2-bis(3-methoxy-4-hydroxyphenyl)propane,
2-(4-hydroxyphenyl)-2-(3-methoxy-4-hydroxyphenyl)propane,
1,1-bis(3-tert-butyl-4-hydroxyphenyl)propane,
2,2-bis(3,5-dimethyl-4-hydroxyphenyl)propane,
2,2-bis(3-cyclohexyl-4-hydroxyphenyl)propane,
2-(4-hydroxyphenyl)-2-(3-cyclohexyl-4-hydroxyphenyl)propane,
α,α'-bis(4-hydroxyphenyl)-1,4-diisopropylbenzene,
1,3-bis[2-(4-hydroxyphenyl)-2-propyl]benzene,
4,4-dihydroxydiphenylmethane,
bis(4-hydroxyphenyl)cyclohexylmethane,
bis(4-hydroxyphenyl)phenylmethane,
bis(4-hydroxyphenyl) (4-propenylphenyl)methane,
bis(4-hydroxyphenyl)diphenylmethane,
bis(4-hydroxyphenyl)naphthylmethane,
1,1-bis(4-hydroxyphenyl)ethane,
1,1-bis(4-hydroxyphenyl)-1-phenylethane,
1,1-bis(4-hydroxyphenyl)-1-naphthylethane,
1,1-bis(4-hydroxyphenyl)butane,
2,2-bis(4-hydroxyphenyl)butane,
2,2-bis(4-hydroxyphenyl)pentane,
2,2-bis(4-hydroxyphenyl)hexane,
2,2-bis(4-hydroxyphenyl)octane,
2,2-bis(4-hydroxyphenyl)hexane,
4,4-bis(4-hydroxyphenyl)heptane, and
2,2-bis(4-hydroxyphenyl)nonane;
bis(hydroxyaryl)cycloalkanes, such as
1,1-bis(4-hydroxyphenyl)cyclopentane,
1,1-bis(4-hydroxyphenyl)cyclohexane,
1,1-bis(4-hydroxyphenyl)-3,3-dimethylcyclohexane,
1,1-bis(4-hydroxyphenyl)-3,4-dimethylcyclohexane,
1,1-bis(4-hydroxyphenyl)-3,5-dimethylcyclohexane, 1,1-bis(4-hydroxyphenyl)-3,3,5-trimethylcyclohexane,
1,1-bis(4-hydroxy-3,5-dimethylphenyl)-3,3,5-trimethylcyclohexane,
1,1-bis(4-hydroxyphenyl)-3-propyl-5-methylcyclohexane,
1,1-bis(4-hydroxyphenyl)-3-tert-butyl-cyclohexane,
1,1-bis(4-hydroxyphenyl)-4-tert-butyl-cyclohexane,
1,1-bis(4-hydroxyphenyl)-3-phenylcyclohexane, and
1,1-bis(4-hydroxyphenyl)-4-phenylcyclohexane;
cardo structure-containing bisphenols, such as
9,9-bis(4-hydroxyphenyl)fluorene and
9,9-bis(4-hydroxy-3-methylphenyl)fluorene;
dihydroxydiaryl sulfides, such as 4,4'-dihydroxydiphenyl sulfide and
4,4'-dihydroxy-3,3'-dimethyldiphenyl sulfide;
dihydroxydiaryl sulfoxides, such as 4,4'-dihydroxydiphenyl sulfoxide and 4,4'-dihydroxy-3,3'-dimethyldiphenyl sulfoxide; and
dihydroxydiaryl sulfones, such as 4,4'-dihydroxydiphenyl sulfone and
4,4'-dihydroxy-3,3'-dimethyldiphenyl sulfone.

These aromatic dihydroxy compounds may be used singly, or two or more thereof may be used in any combination at any ratio.

As the above-described other dihydroxy compound, the following aliphatic dihydroxy compounds may also be used in accordance with the intended purpose. Specific examples of such aliphatic dihydroxy compounds include the followings:

alkanediols, such as ethane-1,2-diol, propane-1,2-diol, propane-1,3-diol, 2,2-dimethylpropane-1,3-diol, 2-methyl-2-propylpropane-1,3-diol, butane-1,4-diol, pentane-1,5-diol, hexane-1,6-diol, and decane-1,10-diol;

cycloalkanediols, such as cyclopentane-1,2-diol, cyclohexane-1,2-diol, cyclohexane-1,4-diol, 1,4-cyclohexane dimethanol, 4-(2-hydroxyethyl)cyclohexanol, and 2,2,4,4-tetramethyl-cyclobutane-1,3-diol;

glycols, such as ethylene glycol, 2,2'-oxydiethanol (i.e. diethylene glycol), triethylene glycol, propylene glycol, and spiroglycol;

aralkyldiols, such as 1,2-benzene dimethanol, 1,3-benzene dimethanol, 1,4-benzene dimethanol, 1,4-benzene diethanol,
1,3-bis(2-hydroxyethoxy)benzene,
1,4-bis(2-hydroxyethoxy)benzene,
2,3-bis(hydroxymethyl)naphthalene,
1,6-bis(hydroxyethoxy)naphthalene, 4,4'-biphenyl dimethanol,
4,4'-biphenyl diethanol, 1,4-bis(2-hydroxyethoxy)biphenyl, bisphenol A-bis(2-hydroxyethyl)ether, and bisphenol S-bis (2-hydroxyethyl) ether;

cyclic ethers, such as 1,2-epoxyethane (i.e. ethylene oxide), 1,2-epoxypropane (i.e. propylene oxide), 1,2-epoxycyclopentane, 1,2-epoxycyclohexane, 1,4-epoxycyclohexane, 1-methyl-1,2-epoxycyclohexane, 2,3-epoxynorbornane, and 1,3-epoxypropane; and oxygen-containing heterocyclic dihydroxy compounds, such as isosorbide, isomannide, and isoidide.

These aliphatic dihydroxy compounds may be used singly, or two or more thereof may be used in any combination at any ratio.

Examples of the carbonate-forming compound to be used include carbonyl halides and carbonate esters. These carbonate-forming compounds may be used singly, or two or more thereof may be used in any combination at any ratio.

Specific examples of the carbonyl halides include phosgene; and haloformates, such as bischloroformates of dihydroxy compounds, and monochloroformates of dihydroxy compounds.

Specific examples of the carbonate esters include compounds represented by the following Formula (6), for example, aryl carbonates; dialkyl carbonates; biscarbonates of dihydroxy compounds; monocarbonates of dihydroxy compounds; and carbonates of dihydroxy compounds, such as cyclic carbonates.

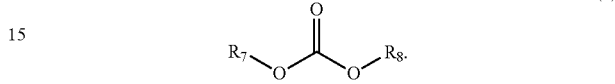

(6)

In Formula (6), $R_7$ and $R_8$ each independently represent an alkyl, aryl or arylalkyl group having 1 to 30 carbon atoms. Hereinafter, when $R_7$ and $R_8$ are each an alky group or an arylalkyl group, the carbonate ester may be referred to as "dialkyl carbonate", and when $R_7$ and $R_8$ are aryl groups, the carbonate ester may be referred to as "diaryl carbonate". Particularly, from the standpoint of reactivity with dihydroxy compounds, both $R_7$ and $R_8$ are preferably aryl groups, and the carbonate ester is more preferably a diaryl carbonate represented by the following Formula (7):

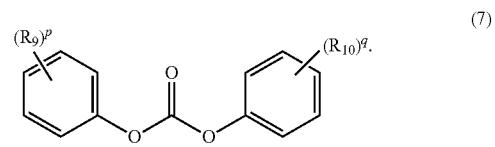

(7)

In Formula (7), $R_9$ and $R_{10}$ each independently represent a halogen atom, a nitro group, a cyano group, an alkyl group having 1 to 20 carbon atoms, an alkoxycarbonyl group having 1 to 20 carbon atoms, a cycloalkyl group having 4 to 20 carbon atoms, or an aryl group having 6 to 20 carbon atoms; and p and q each independently represent an integer of 0 to 5.

Specific examples of such a carbonate ester include dialkyl carbonates, such as dimethyl carbonate, diethyl carbonate, and di-t-butyl carbonate; and (substituted) diaryl carbonates, such as diphenyl carbonate (hereinafter, may be referred to as "DPC"), bis(4-methylphenyl)carbonate, bis(4-chlorophenyl)carbonate, bis(4-fluorophenyl)carbonate, bis (2-chlorophenyl)carbonate, bis(2,4-difluorophenyl)carbonate, bis(4-nitrophenyl)carbonate, bis(2-nitrophenyl) carbonate, bis(methylsalicylphenyl)carbonate, and ditolyl carbonate, among which diphenyl carbonate is preferred. These carbonate esters may be used singly, or in combination of two or more thereof as a mixture.

Preferably 50% by mole or less, more preferably 30% by mole or less of the above-described carbonate esters may be substituted with a dicarboxylic acid or a dicarboxylic acid ester. Representative examples of the dicarboxylic acid or dicarboxylic acid ester include terephthalic acid, isophthalic acid, diphenyl terephthalate, and diphenyl isophthalate. Substitution with any of these dicarboxylic acids and dicarboxylic acid esters yields a polyester carbonate.

As for a method of producing the aromatic polycarbonate resin of the present invention, the aromatic polycarbonate resin of the present invention can be produced by a conventionally known polymerization method, and the polymerization method is not particularly restricted. Examples of the polymerization method include an interfacial polymerization method, a melt transesterification method, a pyridine method, a cyclic carbonate compound ring-opening polymerization method, and a prepolymer solid-phase transesterification method. Among these methods, particularly preferred ones are concretely described below.

Interfacial Polymerization Method

First, a case of producing the aromatic polycarbonate resin of the present invention by an interfacial polymerization method will be described. In an interfacial polymerization method, raw materials, which are an aromatic dihydroxy compound and a carbonate-forming compound (preferably phosgene), are allowed to react in the presence of an aqueous alkali solution and an organic solvent inert to the reaction, usually with the pH being maintained at 9 or higher, and an interfacial polymerization is subsequently carried out in the presence of a polymerization catalyst to obtain a polycarbonate resin. In the reaction system, as required, a molecular weight modifier (chain terminator) may be included and, for inhibition of oxidation of the aromatic dihydroxy compound, an antioxidant may be included as well.

The aromatic dihydroxy compound and the carbonate-forming compound, which are the raw materials, are as described above. Among carbonate-forming compounds, phosgene is preferably used, and a method using phosgene is specifically called "phosgene method".

The organic solvent inert to the reaction is not particularly restricted, and examples thereof include chlorinated hydrocarbons, such as dichloromethane, 1,2-dichloroethane, chloroform, monochlorobenzene, and dichlorobenzene; and aromatic hydrocarbons, such as benzene, toluene, and xylene. These organic solvents may be used singly, or two or more thereof may be used in any combination at any ratio.

Examples of an alkali compound contained in the aqueous alkali solution include, but not particularly limited to: alkali metal compounds, such as sodium hydroxide, potassium hydroxide, lithium hydroxide and sodium bicarbonate, and alkaline earth metal compounds, among which sodium hydroxide and potassium hydroxide are preferred. These alkali compounds may be used singly, or two or more thereof may be used in any combination at any ratio.

The concentration of the alkali compound in the aqueous alkali solution is not restricted; however, the alkali compound is usually used in an amount of 5 to 10% by mass so as to control the pH of the aqueous alkali solution to be 10 to 12 during the reaction. For example, in a case where phosgene is blown into the reaction system, in order to control the pH of the aqueous phase to be 10 to 12, preferably 10 to 11, it is preferred to adjust the molar ratio of the raw material aromatic dihydroxy compound and the alkali compound to be usually 1:1.9 or higher, particularly 1:2.0 or higher, but usually 1:3.2 or lower, particularly 1:2.5 or lower.

The polymerization catalyst is not particularly restricted, and examples thereof include aliphatic tertiary amines, such as trimethylamine, triethylamine, tributylamine, tripropylamine, and trihexylamine; alicyclic tertiary amines, such as N,N'-dimethylcyclohexylamine and N,N'-diethylcyclohexylamine; aromatic tertiary amines, such as N,N'-dimethylaniline and N,N'-diethylaniline; quaternary ammonium salts, such as trimethylbenzyl ammonium chloride, tetramethyl ammonium chloride, and triethylbenzyl ammonium chloride; pyridine; guanine; and salts of guanidine. These polymerization catalysts may be used singly, or two or more thereof may be used in any combination at any ratio.

The molecular weight modifier is not particularly restricted, and examples thereof include aromatic phenols having a monohydric phenolic hydroxyl group; aliphatic alcohols, such as methanol and butanol; mercaptan; and phthalic acid imide, among which aromatic phenols are preferred. Specific examples of such aromatic phenols include phenol, o-n-butylphenol, m-n-butylphenol, p-n-butylphenol, o-isobutylphenol, m-isobutylphenol, p-isobutylphenol, o-t-butylphenol, m-t-butylphenol, p-t-butylphenol, o-n-pentylphenol, m-n-pentylphenol, p-n-pentylphenol, o-n-hexylphenol, m-n-hexylphenol, p-n-hexylphenol, p-t-octylphenol, o-cyclohexylphenol, m-cyclohexylphenol, p-cyclohexylphenol, o-phenylphenol, m-phenylphenol, p-phenylphenol, o-n-nonylphenol, m-nonylphenol, p-n-nonylphenol, o-cumylphenol, m-cumylphenol, p-cumylphenol, o-naphthylphenol, m-naphthylphenol, and p-naphthylphenol; 2,5-di-t-butylphenol; 2,4-di-t-butylphenol; 3,5-di-t-butylphenol; 2,5-dicumylphenol; 3,5-dicumylphenol; p-cresol; bromophenol; tribromophenol; monoalkylphenols having a linear or branched alkyl group having an average carbon number of 12 to 35 at an ortho-position, meta-position, or para-position; 9-(4-hydroxyphenyl)-9-(4-methoxyphenyl)fluorene; 9-(4-hydroxy-3-methylphenyl)-9-(4-methoxy-3-methylphenyl)fluorene; and 4-(1-adamantyl)phenol. Thereamong, p-t-butyl phenol, p-phenylphenol and p-cumylphenol are preferably used. These molecular weight modifiers may be used singly, or two or more thereof may be used in any combination at any ratio.

The amount of the molecular weight modifier to be used is not particularly restricted; however, it is usually not less than 0.5 moles, preferably not less than 1 mole, but usually 50 moles or less, preferably 30 moles or less, with respect to 100 moles of the raw material dihydroxy compound. By using the molecular weight modifier in this range, the thermal stability and the hydrolysis resistance of the aromatic polycarbonate resin can be improved.

In the reaction, a reaction substrate(s) (reaction raw material(s)), a reaction medium/media (organic solvent(s)), a catalyst(s), an additive(s) and the like may be mixed in any order as long as a desired aromatic polycarbonate resin can be obtained, and an appropriate order may be set arbitrarily. For example, in a case where phosgene is used as the carbonate-forming compound, a molecular weight modifier may be mixed at any point between the reaction of a raw material aromatic dihydroxy compound with phosgene (phosgenation) and the start of the polymerization reaction.

The reaction temperature is not particularly restricted; however, it is usually 0 to 40° C. The reaction time is also not particularly restricted; however, it is usually several minutes (e.g., 10 minutes) to several hours (e.g., 6 hours).

Melt Transesterification Method

Next, a case of producing the aromatic polycarbonate resin of the present invention by a melt transesterification method will be described. In a melt transesterification method, a transesterification reaction between, for example, a carbonate ester and a raw material aromatic dihydroxy compound is carried out.

The raw material aromatic dihydroxy compound and the carbonate ester are as described above.

The raw material aromatic dihydroxy compound and the carbonate ester may be used at any ratio as long as a desired aromatic polycarbonate resin can be obtained; however, in the polymerization with the aromatic dihydroxy compound, the carbonate ester is preferably used in an excess amount with respect to the raw material aromatic dihydroxy compound. That is, the amount of the carbonate ester is preferably 1.01 to 1.30 times (molar ratio), more preferably 1.02 to 1.20 times (molar ratio), with respect to the amount of the aromatic dihydroxy compound. When the molar ratio is excessively low, the amount of terminal OH groups in the resulting aromatic polycarbonate resin is increased, and the thermal stability of the resin tends to be deteriorated. Meanwhile, when the molar ratio is excessively high, the transesterification reaction rate is reduced, and this can make it difficult to produce an aromatic polycarbonate resin having a desired molecular weight, or an increased amount of residual carbonate ester in the resulting resin may cause an odor when the resin is molded or made into a molded article.

When the aromatic polycarbonate resin is produced by a melt transesterification method, a transesterification catalyst is usually used. The transesterification catalyst is not particularly restricted, and any conventionally known transesterification catalyst can be used. For example, it is preferred to use an alkali metal compound and/or an alkaline earth metal compound. In addition, a basic compound, such as a basic boron compound, a basic phosphorus compound, a basic ammonium compound or an amine compound, may be supplementarily used in combination. These transesterification catalysts may be used singly, or two or more thereof may be used in any combination at any ratio.

In the melt transesterification method, the reaction temperature is not particularly restricted; however, it is usually 100 to 320° C. The pressure during the reaction is also not particularly restricted; however, the reaction is usually carried out under a reduced pressure of not higher than 2 mmHg. As a specific operation, a melt polycondensation reaction may be carried out under the above-described conditions while removing by-products.

The aromatic polycarbonate resin of the present invention is markedly affected by heat history and oxygen in the presence of an alkali catalyst, and this leads to deterioration of the hue. Therefore, the reaction temperature is preferably not higher than 320° C., and it is preferred to select a reduced pressure condition where the lower limit of the pressure is about 0.05 mmHg so as to prevent oxygen from leaking into the system from an equipment due to an excessive pressure reduction.

As for a reaction mode, the reaction can be carried out by either a batchwise method or a continuous method. When the reaction is carried out in a batchwise mode, a reaction substrate(s), a reaction solvent(s), a catalyst(s), an additive(s) and the like may be mixed in any order as long as a desired aromatic polycarbonate resin can be obtained, and an appropriate order may be set arbitrarily. However, taking into consideration the stability and the like of the resulting aromatic polycarbonate resin, the melt polycondensation reaction is preferably carried out in a continuous mode.

When the melt polycondensation reaction is carried out in a continuous mode, it is preferred to allow the reaction to proceed sequentially in three to five polymerization vessels, depending on the polymerization degree of the reaction solution. This enables to select appropriate conditions, such as the reaction temperature, reaction pressure, stirring power and reactor mode in each polymerization vessel, in accordance with the properties and viscosity of the resin in each polymerization vessel, so that the production efficiency is improved. A method of transferring the reaction solution from each polymerization vessel varies depending on the viscosity of the solution; however, for example, a gear pump is employed.

The melt polycondensation reaction is usually carried out under a reduced pressure condition; therefore, not only the reactors but also the air tightness of the shaft seals and the like of the pumps used for transferring the reaction solution are important. Accordingly, for example, a gland seal which seals a fluid inside each pump using a contact pressure that is derived from a shaft surface-pressing force generated by tightening a packing (gland) inside a stuffing box with a gland clamp, and in which a lantern ring is integrated into the middle of the packing so as to inhibit the inflow of the atmosphere from outside due to, for example, injection of pressure water, a high-viscosity polymer or the like; and a mechanical seal which is constituted by a seal ring capable of moving in the shaft direction by means of a spring or the like and a stationary mating ring (or a floating sheet), and provides sealing by allowing the sliding surfaces of these rings that are perpendicular to the shaft to come into contact and relatively rotate with each other, are employed. It is necessary that these seals ensure slidability with the shaft that is a movable part. An improvement in the air tightness and securing of the slidability are contradictory, and a balance thereof is thus selected in accordance with the use environment to choose an appropriate equipment, structure, and sealing strength. For example, with regard to the gland seal, a setting in which the sealing strength is improved by retightening the gland clamp can be adopted.

In the melt transesterification method, a catalyst deactivator may be used as required. As the catalyst deactivator, any compound that neutralizes the transesterification catalyst may be used. Examples thereof include sulfur-containing acidic compounds and derivatives thereof, and phosphorus-containing acidic compounds and derivatives thereof. These catalyst deactivators may be used singly, or two or more thereof may be used in any combination at any ratio.

The amount of the catalyst deactivator to be used is not particularly restricted; however, it is usually not less than 0.5 equivalents, preferably not less than 1 equivalent, more preferably not less than 3 equivalents, but usually 50 equivalents or less, preferably 10 equivalents or less, more preferably 8 equivalents or less, with respect to the alkali metal or alkaline earth metal contained in the transesterification catalyst. Further, the amount of the catalyst deactivator to be used is usually not less than 1 ppm by mass, but usually 100 ppm by mass or less, preferably 50 ppm by mass or less, with respect to the resulting aromatic polycarbonate resin.

The aromatic polycarbonate resin of the present invention can be mixed with a thermoplastic resin, such as other aromatic polycarbonate resin, within a range that does not markedly deteriorate the effects of the present invention and the desired various physical properties. As the other aromatic polycarbonate resin, an aromatic polycarbonate resin (A-PC) composed of carbonate structural units derived from 2,2-bis(4-hydroxyphenyl)propane is preferably used.

The aromatic polycarbonate resin composition of the present invention may contain other component(s) (resin additive(s)) in addition to the above-described components described above, within a range that does not markedly deteriorate the effects of the present invention and the desired various physical properties. Examples of the resin additives include heat stabilizers, antioxidants, mold release agents, ultraviolet absorbers, flame retardants, brightness improvers, reinforcing agents, antistatic agents, anti-fogging agents, lubricants, anti-blocking agents, dispersants, and antimicrobial agents. Thereamong, for the use as a general injection molding material, the aromatic polycarbonate resin composition of the present invention preferably contains at least one selected from the group consisting of heat stabilizers, antioxidants, dyes, pigments, and mold release agents.

The above-described resin additives may be incorporated singly, or two or more thereof may be incorporated in any combination at any ratio.

EXAMPLES

The present invention will now be described by way of Examples thereof; however, the present invention is not restricted to the following Examples by any means.
(Synthesis Examples of Aromatic Dihydroxy Compound)

Synthesis of 1-bis (4-hydroxyphenyl)dodecane

Phenol (102.1 parts by weight) was melted by heating at 40° C., and p-toluenesulfonic acid (8.25 parts by weight) and pure water (7.03 parts by weight) were added thereto. To the resulting mixture, dodecanal (40.0 parts by weight) was added dropwise over a period of 4 hours. Subsequently, this mixture was aged at 40° C. for 2 hours, and the reaction was quenched with a 25% aqueous sodium hydroxide solution. Toluene and pure water were added to remove inorganic salts, and phenol was subsequently removed from the resulting reaction mixture by vacuum distillation. After removing the solvent by distillation, crystallization was allowed to take place from toluene and heptane, whereby 31.9 parts by weight of a target compound was obtained as a white powder. The thus obtained white powder was measured under the below-described conditions, as a result of which the purity was found to be 99.4%.
(Analysis of Aromatic Dihydroxy Compound)

A sample in an amount of 0.01 parts by mass was dissolved in 1 part by mass of acetonitrile. The thus obtained solution was analyzed using an HPLC analyzer (LC-2010, manufactured by Shimadzu Corporation). The conditions were as follows.

Column: INERTSIL ODS3V (manufactured by GL Sciences Inc.)

Elution solvent: acetonitrile/0.1%-by-mass ammonium acetate solution

Detector: UV (254 nm)

Example 1

Bisphenol A and 1,1-bis(4-hydroxyphenyl)dodecane were dissolved in molten diphenyl carbonate, followed by mixing at 140° C. for 9.5 hours under a nitrogen atmosphere. At this point, the thus obtained mixed melt had the following composition: 45.5% by weight of diphenyl carbonate, 32.7% by weight of bisphenol A, and 21.8% by weight of 1,1-bis (4-hydroxyphenyl)dodecane. As an alkali catalyst, 0.3% by weight of a 0.04%-by-weight aqueous cesium carbonate solution was added thereto, and the resultant was continuously loaded to a first polymerization vessel (a stirring blade-equipped tank reactor).

The reaction product in the first polymerization vessel was continuously transferred to a second polymerization vessel (a stirring blade-equipped tank reactor) such that the average retention time in the first polymerization vessel was 50 minutes. Subsequently, the reaction product in the second polymerization vessel was continuously transferred to a third polymerization vessel (a stirring blade-equipped tank reactor) such that the average retention time in the second polymerization vessel was 40 minutes. Further, the reaction product in the third polymerization vessel was continuously transferred to a fourth polymerization vessel (a spectacle blade-equipped horizontal reactor) such that the average retention time in the third polymerization vessel was 50 minutes. The reaction product in the fourth polymerization vessel was continuously extracted such that the average retention time in the fourth polymerization vessel was 115 minutes, and subsequently introduced, while being in a molten state, to an extruder (TEX30α manufactured by The Japan Steel Works, Ltd.; diameter=32 mm, L/D=42, biaxial unidirectional rotary type) connected to the polymerization vessel via a pipe.

For deactivation of the alkali catalyst in the extruder, butyl p-toluenesulfonate was added in an amount of 11.2 equivalents with respect to cesium carbonate, and IRGANOX 1010 was added as an antioxidant in an amount of 1,000 ppm by mass with respect to the resulting aromatic polycarbonate resin, after which the resultant was mixed to obtain a target aromatic polycarbonate resin. The reaction temperature and the reaction pressure in each polymerization vessel were as shown in Table 1.

The physical properties of the thus obtained aromatic polycarbonate resin are shown in Table 1.

Example 2

An aromatic polycarbonate resin was produced in the same manner as in Example 1, except that, with regard to a gear pump for delivering the molten reaction product from the third polymerization vessel to the fourth polymerization vessel, a gland packing of a shaft sealing part was retightened by rotating a gland clamp by ¼.

The physical properties of the thus obtained aromatic polycarbonate resin are shown in Table 1.

Example 3

An aromatic polycarbonate resin was produced in the same manner as in Example 2, except that the temperature of the third polymerization vessel and that of the fourth polymerization vessel were set at 240° C.

The physical properties of the thus obtained aromatic polycarbonate resin are shown in Table 1.

Example 4

An aromatic polycarbonate resin was produced in the same manner as in Example 3, except that the amounts of diphenyl carbonate, bisphenol A and 1,1-bis(4-hydroxyphenyl)dodecane were changed to 45.7% by weight, 32.6% by weight and 21.7% by weight, respectively, and the duration of the melt mixing performed at 140° C. under a nitrogen atmosphere was changed to 15 hours.

The physical properties of the thus obtained aromatic polycarbonate resin are shown in Table 1.

Example 5

Bisphenol A and 1,1-bis(4-hydroxyphenyl)dodecane were dissolved in molten diphenyl carbonate, followed by mixing at 140° C. for 10 hours under a nitrogen atmosphere. At this point, the thus obtained mixed melt had the following composition: 45.4° by weight of diphenyl carbonate, 32.8° by weight of bisphenol A, and 21.8° by weight of 1,1-bis (4-hydroxyphenyl)dodecane. As an alkali catalyst, 0.38 by weight of a 0.046-by-weight aqueous cesium carbonate solution was added thereto, and the resultant was continuously loaded to the first polymerization vessel.

The reaction product in the first polymerization vessel was continuously transferred to the second polymerization vessel such that the average retention time in the first polymerization vessel was 60 minutes. Subsequently, the reaction product in the second polymerization vessel was continuously transferred to the third polymerization vessel such that the average retention time in the second polymerization vessel was 50 minutes. Further, the reaction product in the third polymerization vessel was continuously transferred to the fourth polymerization vessel such that the average retention time in the third polymerization vessel was 55 minutes. It is noted here that the conditions of a gear pump used for delivering the reaction product from the third polymerization vessel to the fourth polymerization vessel were the same as in Example 1. The reaction product in the fourth polymerization vessel was continuously extracted such that the average retention time in the fourth polymerization vessel was 125 minutes, and subsequently introduced, while being in a molten state, to the extruder connected to the polymerization vessel via a pipe.

For deactivation of the alkali catalyst in the extruder, butyl p-toluenesulfonate was added in an amount of 11.2 equivalents with respect to cesium carbonate, and IRGANOX 1010 was added as an antioxidant in an amount of 1,000 ppm by mass with respect to the resulting aromatic polycarbonate resin, after which the resultant was mixed to obtain a target aromatic polycarbonate resin. The reaction temperature and the reaction pressure in each polymerization vessel were as shown in Table 1.

The physical properties of the thus obtained aromatic polycarbonate resin are shown in Table 1.

Comparative Example 1

Bisphenol A and 1,1-bis(4-hydroxyphenyl)dodecane were dissolved in molten diphenyl carbonate, followed by mixing at 140° C. for 10 hours under a nitrogen atmosphere. At this point, the thus obtained mixed melt had the following composition: 45.2% by weight of diphenyl carbonate, 32.9% by weight of bisphenol A, and 21.9% by weight of 1,1-bis(4-hydroxyphenyl)dodecane. As an alkali catalyst, 0.3% by weight of a 0.04%-by-weight aqueous cesium carbonate solution was added thereto, and the resultant was continuously loaded to the first polymerization vessel.

The reaction product in the first polymerization vessel was continuously transferred to the second polymerization vessel such that the average retention time in the first polymerization vessel was 70 minutes. Subsequently, the reaction product in the second polymerization vessel was continuously transferred to the third polymerization vessel such that the average retention time in the second polymerization vessel was 60 minutes. Further, the reaction product in the third polymerization vessel was continuously transferred to the fourth polymerization vessel such that the average retention time in the third polymerization vessel was 70 minutes. It is noted here that the conditions of a gear pump used for delivering the reaction product from the third polymerization vessel to the fourth polymerization vessel were the same as in Example 1. The reaction product in the fourth polymerization vessel was continuously extracted such that the average retention time in the fourth polymerization vessel was 140 minutes, and subsequently introduced, while being in a molten state, to the extruder connected to the polymerization vessel via a pipe.

For deactivation of the alkali catalyst in the extruder, butyl p-toluenesulfonate was added in an amount of 11.2 equivalents with respect to cesium carbonate, and IRGANOX 1010 was added as an antioxidant in an amount of 1,000 ppm by mass with respect to the resulting aromatic polycarbonate resin, after which the resultant was mixed to obtain a target aromatic polycarbonate resin. The reaction temperature and the reaction pressure in each polymerization vessel were as shown in Table 1.

The physical properties of the thus obtained aromatic polycarbonate resin are shown in Table 1.

The "air tightness of equipment", which represents the air tightness of an equipment used in the reaction process, was evaluated based on the following criteria. The air tightness of each equipment used in Examples and Comparative Example is shown in Table 1.

○: An air tightness level sufficient for the production of a common bisphenol-A polycarbonate ◎: An air tightness level further enhanced from that of the above "○"

TABLE 1

| | | | Example 1 | Example 2 | Example 3 | Example 4 | Example 5 | Comparative Example 1 |
|---|---|---|---|---|---|---|---|---|
| Compound of Formula (2) in raw material aromatic dihydroxy compound | | ppm by mass | 49 | 55 | 49 | 49 | 31 | 37 |
| Raw material preparation Vessel | Temperature | ° C. | 140 | 140 | 140 | 140 | 140 | 140 |
| | Retention time | h | 9.5 | 9.5 | 9.5 | 15 | 10 | 10 |
| First polymerization vessel | Temperature | ° C. | 220 | 220 | 220 | 220 | 220 | 220 |
| | Pressure | kPa | 13.3 | 13.3 | 13.3 | 13.3 | 13.3 | 13.3 |
| Second polymerization vessel | Temperature | ° C. | 240 | 240 | 240 | 240 | 240 | 240 |
| | Pressure | kPa | 4 | 4 | 4 | 4 | 4 | 4 |
| Third polymerization vessel | Temperature | ° C. | 245 | 245 | 240 | 240 | 250 | 250 |
| | Pressure | Pa | 200 | 200 | 200 | 200 | 200 | 200 |
| Fourth polymerization vessel | Temperature | ° C. | 245 | 245 | 240 | 240 | 250 | 250 |
| | Pressure | Pa | 80 | 80 | 80 | 80 | 80 | 80 |
| Retention time in reaction process | | min | 255 | 255 | 255 | 255 | 290 | 340 |
| Air tightness of equipment | | | ○ | ◎ | ◎ | ◎ | ○ | ○ |
| Extruder | Inlet temperature | ° C. | 230 | 230 | 230 | 230 | 230 | 230 |
| | Temperature at position of deactivator addition | ° C. | 280 | 280 | 280 | 280 | 280 | 280 |
| | Temperature at position of antioxidant addition | ° C. | 241 | 241 | 241 | 241 | 241 | 241 |
| | Outlet temperature | ° C. | 175 | 175 | 175 | 175 | 175 | 175 |

TABLE 1-continued

|  |  |  | Example 1 | Example 2 | Example 3 | Example 4 | Example 5 | Comparative Example 1 |
|---|---|---|---|---|---|---|---|---|
| Polymer analysis | Q value | $10^{-2}$ cm$^3$/sec | 47.6 | 44.5 | 49.4 | 47.9 | 46.8 | 31.3 |
|  | Viscosity-average molecular weight (Mv) |  | 14,600 | 15,100 | 14,400 | 14,500 | 14,700 | 15,400 |
|  | Amount of terminal hydroxyl groups | ppm by mass | 971 | 980 | 856 | 760 | 988 | 843 |
|  | Compound of Formula (2) | ppm by mass | 108 | 74 | 45 | 51 | 174 | 264 |
| Pellet Y.I. |  |  | 3.33 | 2.27 | 0.51 | 0.77 | 4.92 | 6.89 |

Reference Example 1

Bisphenol A was dissolved in molten diphenyl carbonate, followed by mixing at 140° C. for 9 hours under a nitrogen atmosphere. At this point, the thus obtained mixed melt had the following composition: 49.0% by weight of diphenyl carbonate and 51.0% by weight of bisphenol A. As an alkali catalyst, 0.15% by weight of a 0.04%-by-weight aqueous cesium carbonate solution was added thereto, and the resultant was continuously loaded to the first polymerization vessel.

The reaction product in the first polymerization vessel was continuously transferred to the second polymerization vessel such that the average retention time in the first polymerization vessel was 55 minutes. Subsequently, the reaction product in the second polymerization vessel was continuously transferred to the third polymerization vessel such that the average retention time in the second polymerization vessel was 50 minutes. Further, the reaction product in the third polymerization vessel was continuously transferred to the fourth polymerization vessel such that the average retention time in the third polymerization vessel was 50 minutes. It is noted here that the conditions of a gear pump used for delivering the reaction product from the third polymerization vessel to the fourth polymerization vessel were the same as in Example 1. The reaction product in the fourth polymerization vessel was continuously extracted such that the average retention time in the fourth polymerization vessel was 110 minutes, and subsequently introduced, while being in a molten state, to the extruder connected to the polymerization vessel via a pipe.

For deactivation of the alkali catalyst in the extruder, butyl p-toluenesulfonate was added in an amount of 11.2 equivalents with respect to cesium carbonate, after which the resultant was mixed to obtain a target aromatic polycarbonate resin. The reaction temperature and the reaction pressure in each polymerization vessel were as shown in Table 2.

The physical properties of the thus obtained aromatic polycarbonate resin are shown in Table 2.

Reference Example 2

An aromatic polycarbonate resin was produced in the same manner as in Reference Example 1, except that, with regard to a gear pump for delivering the molten reaction product from the third polymerization vessel to the fourth polymerization vessel, a gland packing of a shaft sealing part was retightened by rotating a gland clamp by ¼.

The physical properties of the thus obtained aromatic polycarbonate resin are shown in Table 2.

TABLE 2

|  |  |  | Reference Example 1 | Reference Example 2 |
|---|---|---|---|---|
| Raw material preparation vessel | Temperature | ° C. | 140 | 140 |
|  | Retention time | h | 9.5 | 9.5 |
| First polymerization vessel | Temperature | ° C. | 220 | 220 |
|  | Pressure | kPa | 13.3 | 13.3 |
| Second polymerization vessel | Temperature | ° C. | 260 | 260 |
|  | Pressure | kPa | 4 | 4 |
| Third polymerization vessel | Temperature | ° C. | 262 | 262 |
|  | Pressure | Pa | 200 | 200 |
| Fourth polymerization vessel | Temperature | ° C. | 260 | 260 |
|  | Pressure | Pa | 80 | 80 |
| Retention time in reaction process |  | min | 265 | 265 |
| Extruder | Inlet temperature | ° C. | 230 | 230 |
|  | Temperature at position of deactivator addition | ° C. | 280 | 280 |
|  | Temperature at position of antioxidant addition | ° C. | 275 | 275 |
|  | Outlet temperature | ° C. | 260 | 260 |
| Polymer analysis | Q value | $10^{-2}$ cm$^3$/sec | 22.4 | 25.4 |
|  | Viscosity-average molecular weight (Mv) |  | 12,500 | 12,220 |
|  | Amount of terminal hydroxyl groups | ppm by mass | 801 | 971 |
| Pellet Y.I. |  |  | 2.25 | 2.16 |

From the results shown in Tables 1 and 2, it was revealed that the hue of an aromatic polycarbonate resin is markedly deteriorated by the effect of heat history in the presence of an alkali catalyst and the effect of air existing in such an extremely small amount that does not affect the production of a generally well-known bisphenol A-type aromatic polycarbonate resin. However, it is difficult to quantify all of these elements and, as a result of intensive studies, the present inventors discovered that the effects on the hue can be quantified based on the content of a compound represented by the following Formula (2) that is detected in a hydrolysate generated by hydrolysis of the subject aromatic polycarbonate resin.

In other words, another aspect of the present invention is a method of producing an aromatic polycarbonate resin containing a structural unit represented by Formula (1), the method including the step of polymerizing an aromatic dihydroxy compound and a carbonate-forming compound such that a hydrolysate obtained by hydrolysis of the aromatic polycarbonate resin contains an aromatic dihydroxy compound represented by Formula (2) and an aromatic dihydroxy compound represented by Formula (3), and that the content of the aromatic dihydroxy compound represented by Formula (2) in the hydrolysate is 250 ppm by mass or less with respect to that of the aromatic dihydroxy compound represented by Formula (3):

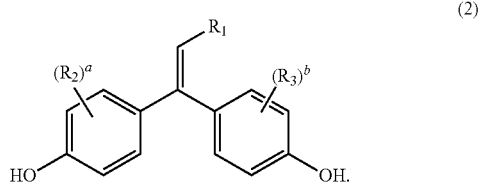

(2)

Example 6

After mixing 5.67 kg of diphenyl carbonate, 4.02 kg of bisphenol A and 2.68 kg of 1,1-bis(4-hydroxyphenyl)dodecane, a 2%-by-weight aqueous cesium carbonate solution was further added as a catalyst such that cesium carbonate was incorporated in an amount of 0.75 μmol per 1 mol of all dihydroxy compounds, whereby a raw material mixture was prepared. This mixture was subsequently loaded to a first reactor having a capacity of 200 L, which was equipped with a stirrer, a heating medium jacket, a vacuum pump, and a reflux condenser. The amount of a compound represented by Formula (2) in 1,1-bis(4-hydroxyphenyl)dodecane used in this process was 3 ppm by mass.

Next, an operation of reducing the pressure inside the first reactor to 1.33 kPa (10 Torr) and then restoring the pressure with nitrogen to an atmospheric pressure was repeated five times to purge the inside of the first reactor with nitrogen. Subsequently, the internal temperature of the first reactor was slowly increased by passing a 230° C. heating medium through the heating medium jacket, and the mixture was thereby dissolved. Then, the stirrer was rotated at 300 rpm, and the temperature inside the heating medium jacket was controlled to maintain the internal temperature of the first reactor at 220° C. Further, the pressure inside the first reactor was reduced from 101.3 kPa (760 Torr) to 13.3 kPa (100 Torr) in terms of absolute pressure over a period of 40 minutes, while distilling away phenol generated as a by-product of oligomerization reaction between the dihydroxy compounds and DPC in the first reactor.

Thereafter, a transesterification reaction was allowed to proceed for 80 minutes, with the pressure inside the first reactor being maintained at 13.3 kPa and phenol being continuously distilled away. The pressure in the system was restored with nitrogen back to 101.3 kPa in terms of absolute pressure and then increased to 0.2 MPa in terms of gauge pressure, after which the resulting oligomer in the first reactor was pressure-transferred to a second reactor through a transfer pipe that had been heated to 200° C. or higher in advance. It is noted here that the second reactor had a capacity of 200 L and was equipped with a stirrer, a heating medium jacket, a vacuum pump, and a reflux condenser. The internal pressure of the second reactor was controlled at an atmospheric pressure, and the internal temperature was controlled at 240° C.

Next, the oligomer pressure-transferred to the second reactor was stirred at 38 rpm, the internal temperature was increased using the heating medium jacket, and the pressure inside the second reactor was reduced from 101.3 kPa to 13.3 kPa in terms of absolute pressure over a period of 40 minutes. Subsequently, the internal temperature was continuously increased, and the internal pressure was further reduced from 13.3 kPa to 399 Pa (3 Torr) in terms of absolute pressure over a period of 40 minutes, while removing distilled phenol out of the system. The internal pressure was further continuously increased and, once the absolute pressure in the second reactor reached 70 Pa (about 0.5 Torr), this pressure of 70 Pa was maintained and a polycondensation reaction was allowed to proceed. The final internal temperature of the second reactor was 250° C. The polycondensation reaction was terminated when the stirring power of the stirrer in the second reactor reached a predetermined level, and the pressure inside the reactor was subsequently restored with nitrogen. Thereafter, a pressure was applied to extract the reaction product from the bottom of the reactor, and the thus recovered product was cooled in a water cooling tank and then made into the form of a strand, which was subsequently cut using a pelletizer, whereby a pellet-form aromatic polycarbonate resin was obtained. The reaction time in the second reactor was 187 minutes. The physical properties of the thus obtained polycarbonate resin are shown in Table 3.

Example 7

An aromatic polycarbonate was produced in the same manner as in Example 6, except that the amount of the compound represented by Formula (2) in 1,1-bis(4-hydroxyphenyl)dodecane was 55 ppm by mass. The reaction time in the second reactor was 155 minutes. The physical properties of the thus obtained polycarbonate resin are shown in Table 3.

Comparative Example 2

After mixing 5.67 kg of diphenyl carbonate, 4.02 kg of bisphenol A and 2.68 kg of 1,1-bis(4-hydroxyphenyl)dodecane, a 2%-by-weight aqueous cesium carbonate solution was further added as a catalyst such that cesium carbonate was incorporated in an amount of 0.75 μmol per 1 mol of all dihydroxy compounds, whereby a raw material mixture was prepared. This mixture was subsequently loaded to a first reactor having a capacity of 200 L, which was equipped with a stirrer, a heating medium jacket, a vacuum pump, and a reflux condenser. The amount of a compound represented by the below-described Formula (2) in 1,1-bis (4-hydroxyphenyl) dodecane used in this process was less than 1 ppm by mass.

Next, an operation of reducing the pressure inside the first reactor to 1.33 kPa (10 Torr) and then restoring the pressure with nitrogen to an atmospheric pressure was repeated five times to purge the inside of the first reactor with nitrogen. Subsequently, the internal temperature of the first reactor was slowly increased by passing a 230° C. heating medium through the heating medium jacket, and the mixture was thereby dissolved. Then, the stirrer was rotated at 300 rpm, and the temperature inside the heating medium jacket was controlled to maintain the internal temperature of the first reactor at 220° C. Further, the pressure inside the first reactor was reduced from 101.3 kPa (760 Torr) to 13.3 kPa (100 Torr) in terms of absolute pressure over a period of 40 minutes; however, phenol distillation was hardly observed, and a target aromatic polycarbonate resin was not obtained.

TABLE 3

|  |  | Example 6 | Example 7 |
| --- | --- | --- | --- |
| Q value | $10^{-2}$ cm$^3$/sec | 55 | 51 |
| Viscosity-average molecular weight (Mv) |  | 14,700 | 14,760 |
| Amount of terminal hydroxyl groups | ppm by mass | 688 | 718 |
| Pellet Y.I. |  | 2.0 | 1.4 |

As described above, a compound represented by the following Formula (3) is likely to be affected by heat history and oxygen in the presence of an alkali catalyst. This is also the same in the process of producing an aromatic hydroxy compound. Accordingly, the absence of a compound represented by the following Formula (2) in the resulting aromatic hydroxy compound suggests the presence of a residual acid component during the production, and it is believed that this acid component deactivates an alkali catalyst in the process of producing an aromatic polycarbonate compound. In the process manufacturing for an aromatic polycarbonate compound, such a deactivating effect caused by an acid component can be mitigated by adding an excess amount of an alkali catalyst; however, this is not preferred since an excess amount of an alkali catalyst leads to deterioration of the physical properties of the resulting aromatic polycarbonate compound. By the present results, it was revealed to be useful to pay attention to a compound of the following Formula (2) also in the quality control of a raw material aromatic hydroxy compound.

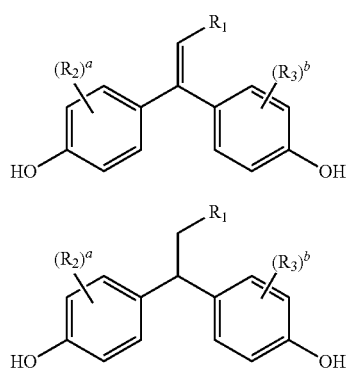

What is claimed is:

1. An aromatic polycarbonate resin, comprising a structural unit represented by the following Formula (1), that is derived from an aromatic dihydroxy starting compound and a carbonate-forming starting compound, wherein:
a hydrolysate obtained by hydrolysis of the aromatic polycarbonate resin comprises aromatic dihydroxy compounds represented by the following Formulae (2) and (3);
a content of the aromatic dihydroxy compound represented by the following Formula (2) in the hydrolysate is 250 ppm by mass or less with respect to that of the aromatic dihydroxy compound represented by the following Formula (3); and

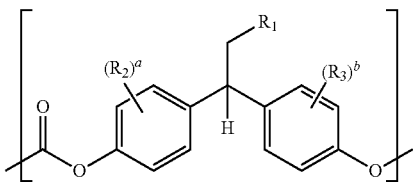

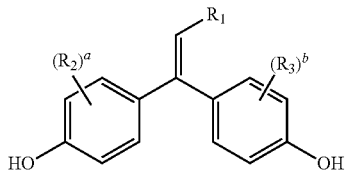

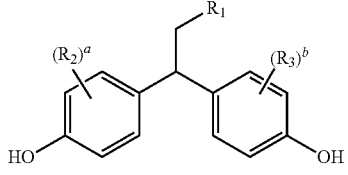

$R_1$ represents an alkyl group having 1 to 24 carbon atoms; $R_2$ and $R_3$ each independently represent a monovalent hydrocarbon group having 1 to 15 carbon atoms; and a and b each independently represent an integer of 0 to 4.

2. The aromatic polycarbonate resin according to claim 1, having a viscosity-average molecular weight of 9,000 or higher.

3. The aromatic polycarbonate resin according to claim 1, wherein the content of the aromatic dihydroxy compound represented by the Formula (2) in the hydrolysate is not less than 1 ppm by mass with respect to that of the aromatic dihydroxy compound represented by the Formula (3).

4. The aromatic polycarbonate resin according to claim 1, wherein, in the Formulae (1) to (3), $R_1$ represents an alkyl group having 6 to 24 carbon atoms.

5. A method of producing the aromatic polycarbonate resin according to claim 1, the method comprising the polymerization step of polymerizing the aromatic dihydroxy compound and the carbonate-forming compound in the presence of an alkali catalyst.

6. The method of producing the aromatic polycarbonate resin according to claim 5, wherein the polymerization step is performed by a transesterification method.

7. The method of producing the aromatic polycarbonate resin according to claim 6, wherein, in the polymerization step, a transesterification catalyst is deactivated after a transesterification reaction, without substantial solidification of the resulting aromatic polycarbonate resin.

8. The method of producing the aromatic polycarbonate resin according to claim 7, wherein, in the polymerization step, a deactivator is added in an amount of not less than 3 equivalents and 50 equivalents or less with respect to the transesterification catalyst.

9. An aromatic dihydroxy compound, comprising aromatic dihydroxy compounds represented by the following Formulae (2) and (3), wherein the content of the aromatic dihydroxy compound represented by Formula (2) is 250 ppm by mass or less:

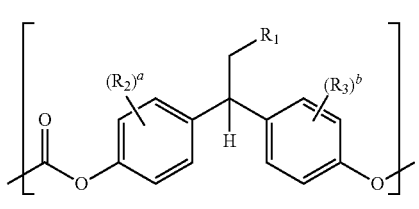

(1)

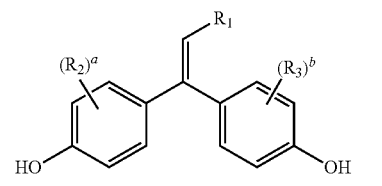

(2)

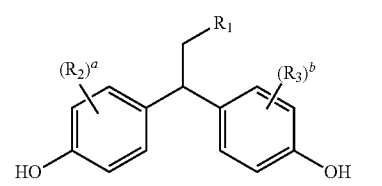

(3)

R₁ represents an alkyl group having 1 to 24 carbon atoms; R₂ and R₃ each independently represent a monovalent hydrocarbon group having 1 to 15 carbon atoms; and a and b each independently represent an integer of 0 to 4.

14. The aromatic polycarbonate resin according to claim 1, wherein R₁ is n-undecyl.

15. The aromatic polycarbonate resin according to claim 1, wherein R₂ and R₃ are each hydrogen.

16. The aromatic polycarbonate resin according to claim 1, wherein the aromatic dihydroxy compound represented by Formula (3) is 1,1-bis(4-hydroxyphenyl)dodecane.

17. The aromatic polycarbonate resin according to claim 1, wherein the the aromatic dihydroxy compound represented by Formula (2) present in the hydrolysate is 100 ppm by mass or less.

18. The method of claim 13, wherein R₁ is n-undecyl.

19. The method of claim 13, wherein the aromatic dihydroxy compound represented by Formula (3) is 1,1-bis(4-hydroxyphenyl)dodecane.

20. The method of claim 13, wherein the hydrolysis of the aromatic polycarbonate resin comprises:
dissolving the aromatic polycarbonate resin in a liquid mixture of dicyclomethan, methanol, and aqueous sodium hydroxide solution to form a mixture; and
heating the mixture at 75° C. for 30 minutes.

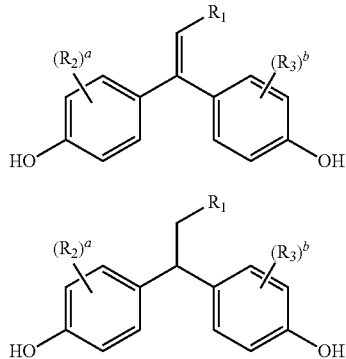

(2)

(3)

wherein, R₁ represents an alkyl group having 1 to 24 carbon atoms; R₂ and R₃ each independently represent a monovalent hydrocarbon group having 1 to 15 carbon atoms; and a and b each independently represent an integer of 0 to 4.

10. The aromatic dihydroxy compound according to claim 9, wherein the content of the aromatic dihydroxy compound represented by the Formula (2) is not less than 1 ppm by mass.

11. The aromatic dihydroxy compound according to claim 9, wherein, in the Formulae (2) and (3), R₁ represents an alkyl group having 6 to 24 carbon atoms.

12. An aromatic polycarbonate resin composition, comprising the aromatic polycarbonate resin according to claim 1,
wherein the aromatic polycarbonate resin composition further comprises an aromatic polycarbonate resin composed of carbonate structural units derived from 2,2-bis(4-hydroxyphenyl)propane.

13. A method of producing an aromatic polycarbonate resin comprising a structural unit represented by the following Formula (1), the method comprising the step of polymerizing an aromatic dihydroxy starting compound and a carbonate-forming starting compound, wherein:
a hydrolysate obtained by hydrolysis of the aromatic polycarbonate resin comprises aromatic dihydroxy compounds represented by the following Formulae (2) and (3), and a content of the aromatic dihydroxy compound represented by the following Formula (2) in the hydrolysate is 250 ppm by mass or less with respect to that of the aromatic dihydroxy compound represented by the following Formula (3), and